(12) United States Patent
Sunaga et al.

(10) Patent No.: US 11,597,910 B2
(45) Date of Patent: Mar. 7, 2023

(54) MEDICAL INSTRUMENT, CELL CULTURE METHOD, FLUORINE-CONTAINING CYCLIC OLEFIN POLYMER AND FLUORINE-CONTAINING CYCLIC OLEFIN POLYMER COMPOSITION FOR IT, AND CULTURED CELLS

(71) Applicant: MITSUI CHEMICALS, INC., Tokyo (JP)

(72) Inventors: Tadahiro Sunaga, Sodegaura (JP); Takashi Oda, Sodegaura (JP); Hiroshi Miyasako, Mobara (JP); Takeshi Osaka, Mobara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 366 days.

(21) Appl. No.: 15/502,507

(22) PCT Filed: Aug. 10, 2015

(86) PCT No.: PCT/JP2015/072631
§ 371 (c)(1),
(2) Date: Feb. 8, 2017

(87) PCT Pub. No.: WO2016/024566
PCT Pub. Date: Feb. 18, 2016

(65) Prior Publication Data
US 2017/0233696 A1    Aug. 17, 2017

(30) Foreign Application Priority Data

Aug. 13, 2014 (JP) ............................. JP2014-164912
Feb. 4, 2015 (JP) ............................. JP2015-019996

(51) Int. Cl.
*C12N 5/00* (2006.01)
*C12M 1/00* (2006.01)
*C12M 1/12* (2006.01)

(52) U.S. Cl.
CPC ............ *C12N 5/0068* (2013.01); *C12M 23/02* (2013.01); *C12M 23/20* (2013.01); *C12M 25/06* (2013.01); *C12M 47/02* (2013.01); *C12M 47/04* (2013.01)

(58) Field of Classification Search
CPC ..... C12N 5/0068; C12M 23/02; C12M 47/02; C12M 23/20; C12M 25/06; C12M 47/04
See application file for complete search history.

(56) References Cited

U.S. PATENT DOCUMENTS 7,727,759 B2    6/2010   Ozawa et al.
8,263,129 B2 *  9/2012   DeSimone ........... A61K 9/0097
                                                      424/489

(Continued)

FOREIGN PATENT DOCUMENTS

CN    103159914 A    6/2013
CN    103476804 A    12/2013

(Continued)

OTHER PUBLICATIONS

N. Pereira Rodrigues, Y. Sakai and T. Fujii, Cell-Based Microfluidic Biochip for the Electrochemical Real-Time Monitoring of Glucose and Oxygen, 2008, Sensors and Actuators B: Chemical, vol. 132, pp. 608-613 (Year: 2008).*

(Continued)

*Primary Examiner* — David W Berke-Schlessel
*Assistant Examiner* — Trent R Clarke
(74) *Attorney, Agent, or Firm* — Buchanan, Ingersoll & Rooney PC

(57) ABSTRACT

Medical instrument includes a substrate, in which cells are in contact with or held on a surface of the substrate, and at (Continued)

least the surface of the substrate which holds the cells is formed of a fluorine-containing cyclic olefin polymer which contains a repeating structure unit represented by Formula (1),

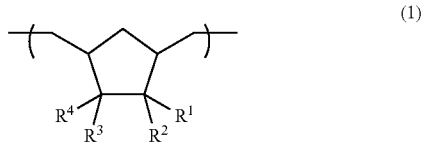

(1)

wherein in Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine, $R^1$ to $R^4$ are selected from hydrogen and certain non-fluorinated groups when $R^1$ to $R^4$ do not contain fluorine, $R^1$ to $R^4$ may be the same as or different from each other, and $R^1$ to $R^4$ may be bonded to each other to form a cyclic structure.

3 Claims, 3 Drawing Sheets

(56) References Cited

U.S. PATENT DOCUMENTS

| | | | |
|---|---|---|---|
| 9,056,938 | B2 | 6/2015 | Sunaga et al. |
| 9,394,514 | B2 | 7/2016 | Takahashi et al. |
| 9,428,721 | B2 | 8/2016 | Taniguchi et al. |
| 2004/0125266 | A1* | 7/2004 | Miyauchi .......... B01L 3/502761 349/57 |
| 2005/0153438 | A1* | 7/2005 | Shirasu .................. C12M 23/20 435/293.1 |
| 2005/0287111 | A1 | 12/2005 | Schlenoff et al. |
| 2006/0234377 | A1* | 10/2006 | Okano ................ A61L 27/3891 435/368 |
| 2009/0246872 | A1 | 10/2009 | Ozawa et al. |
| 2010/0316842 | A1* | 12/2010 | Tuteja .................... D01D 5/003 428/143 |
| 2011/0045500 | A1 | 2/2011 | Taniguchi et al. |
| 2012/0100612 | A1 | 4/2012 | Takahashi et al. |
| 2012/0156448 | A1 | 6/2012 | Sunaga et al. |
| 2014/0037900 | A1 | 2/2014 | Takihara et al. |
| 2015/0274954 | A1 | 10/2015 | Sunaga et al. |
| 2018/0086864 | A1 | 3/2018 | Sunaga et al. |

FOREIGN PATENT DOCUMENTS

| | | |
|---|---|---|
| EP | 3279308 A1 | 2/2018 |
| JP | 7-047105 A | 2/1995 |
| JP | 2004-129558 A | 4/2004 |
| JP | 2004-147585 A | 5/2004 |
| JP | 2007-177046 A | 7/2007 |
| JP | 2008-306977 A | 12/2008 |
| JP | 2010-088347 A | 4/2010 |
| WO | WO 2007/097121 A1 | 8/2007 |
| WO | WO 2009/099152 A1 | 8/2009 |
| WO | WO 2010/150521 A1 | 12/2010 |
| WO | WO 2011/024421 A1 | 3/2011 |

OTHER PUBLICATIONS

Natanel Korin, Avishay Bransky, Maria Khoury, Uri Dinnar, Shulamit Levenberg, Design of Well and Groove Microchannel Bioreactors for Cell Culture, 2009, Biotechnol. Bioeng. vol. 102, pp. 1222-1230 (Year: 2009).*
Elisa Figallo, Christopher Cannizzaro, Sharon Gerecht, Jason A. Burdick, Robert Langer, Nicola Elvassore and Gordana Vunjak-Novakovic, Micro-bioreactor array for controlling cellular microenvironments, 2007, Lab on a Chip, vol. 7, pp. 710-719 (Year: 2007).*
Kangning Ren, Wen Dai, Jianhua Zhou, Jing Su, and Hongkai Wu, Whole-Teflon microfluidic chips, 2011, PNAS, vol. 108, No. 20, pp. 8162-8166 (Year: 2011).*
International Search Report (PCT/ISA/210) dated Oct. 13, 2015, by the Japanese Patent Office as the International Searching Authority for International Application No. PCT/JP2015/072631.
Written Opinion (PCT/ISA/237) dated Oct. 13, 2015, by the Japanese Patent Office as the International Searching Authority for International Application No. PCT/JP2015/072631.
Cosmo Bio Co., Ltd., Kogata Kansaibo Baiyo Kit, Jun. 1, 2013,, 2 pages.
Ishida, Yugi et al., "In Vitro Evaluation of Fresh Human Hepatocytes Isolated From Chimeric Mice With Humanized Livers (PXB Mice)", The Journal of Experimental & Applied Cell Culture Research, Jul. 26, 2014, vol. 33, No. 1, p. 103.
Iwane, Hirona et al., "PLLA-KEI Kyojugotai No Micro-So Bunri O Riyo Shita Biointerface No Seigyo", Polymer Preprints, Japan, 2013, vol. 62, No. 1, p. 1823.
Kitamura, Akane et al., "Ion Beam Shosha Ni Yoru Fussokei Kobunshi Zairyo Hyome No Keijo Jiko Soshikika Seigyo", Dai 13 Kai Hoshasen Process Symposium, Nov. 12, 2009, 1 page.
Kuwabara, Kosuke, "Nanoimprint Ni Yoru Bisai Kako To Sono Oyo Tenkai", Kyoto University, Thesis or Dissertation, Mar. 23, 2011, pp. 1-107.
Sano, Seigo et al., "Acetaminophen-Induced Hepatotoxicity in Three-Dimensional Culture System With Rat Hepatocytes" Dai 40 Kai Annual Meeting of the Japanese Society of Toxicology Session, Aug. 14, 2013, entire text.
Sugiyama, Kazuo et al., "Preparation of Poly(Methyl Methacrylate-CO-1H, 1H, 7H-Dodecafluoroheptyl Methacrylate) Microspheres as Biomedical Materials", Kinki University Research Institute of Fundamental Technology for Next Generation Hokoku, 2012, vol. 3, pp. 39-46.
Tamada, Yasushi et al., "Effect of Preadsorbed Proteins on Cell Adhesion to Polymer Surfaces", Journal of Colloid and Interface Science, 1993, vol. 155, pp. 334-339.
The First Office Action issued by The State Intellectual Property Office of People's Republic of China in corresponding Chinese Patent Application No. 201580043114.7 dated Jun. 5, 2018 (24 pages including partial English translation).
Partial Supplementary Search Report pursuant to Rule 164(1) EPC issued by the European Patent Office in corresponding European Patent Application No. 15832009.3-1132 dated Feb. 19, 2018 (11 pages).
PCT International Preliminary Report on Patentability (IPRP) and Written Opinion dated Feb. 23, 2017, in corresponding International Application No. PCT/JP2015/072631 (26 pages including partial English translation).
Office Action issued by the Taiwanese Patent Office in corresponding Taiwanese Patent Application No. 104126178 dated Mar. 29, 2019 (12 pages).

* cited by examiner

◯: DNA STAINING OF CELL NUCLEI
●: Actine STAINING OF CYTOSKELETON PROTEIN

○ : DNA STAINING OF CELL NUCLEI
● : Actine STAINING OF CYTOSKELETON PROTEIN

○: GREEN FLUORESCENCE EMISSION
   (AUTOFLUORESCENCE) OF DEAD CELLS; 99.98%
   LIVING CELLS

MEDICAL INSTRUMENT, CELL CULTURE METHOD, FLUORINE-CONTAINING CYCLIC OLEFIN POLYMER AND FLUORINE-CONTAINING CYCLIC OLEFIN POLYMER COMPOSITION FOR IT, AND CULTURED CELLS

TECHNICAL FIELD

The present invention relates to medical instrument, a cell culture method, a fluorine-containing cyclic olefin polymer and a fluorine-containing cyclic olefin polymer composition for it, and cultured cells.

BACKGROUND ART

Many flora and fauna cells have been cultured in the related art and various types of culturing techniques have been researched. Cell culturing techniques are techniques which are essential for, in particular, the development of medicine, the investigation of pathological mechanisms, and the like in the field of life science, and in addition to cell culture techniques for research purposes, various types of industrial production culture methods have been researched for the purpose of use in fields such as biology, medical science, pharmaceutical science, and immunology. In addition, in recent years, in fields such as medicine, research has also been actively carried out for culturing tissue cells and using these as substitute tissues for artificial organs, artificial dentary bone, artificial skin, and the like.

In such cell culturing, culturing is normally performed with a culture solution in a certain container. In cell culturing, many animal cells in particular have adhesion-dependency and are attached to a substance to be grown and a substrate (instrument) for attaching the cells is necessary for culturing the cells which have adhesion-dependency. As a substrate for cell culturing, a polystyrene molded product is typical as the main material thereof and substrates on which a low temperature plasma treatment, a corona discharging treatment, or the like are carried out on the surface of the substrate and to which hydrophilicity is imparted are commercially available as culture apparatus such as Petri dishes, flasks, and multi-well plates.

However, it is known that an important property of adherent cell types is contact inhibition in which, in a case of carrying out cell culturing using culture apparatus, cell proliferation stops when the cells cover the culturing surface of the culture container. In addition, a density effect is also known in which, when the concentration of the inoculated cells is excessively low, the adhesion or proliferation of cells is influenced even in an environment in which nutrients, oxygen, and the like are sufficiently supplied to the cells. Furthermore, since cells exhibit an aspect of proliferating in a planar manner while attached to the culture surface of the culture container, as a method which is particularly applied to tissue culturing and in which a cell sheet is produced in a state where a colony is formed by cell proliferation, an operation (referred to below simply as a subculture operation) in which the culturing is carried out by repeating the inoculation of cells is used; however, this operation is complicated and it is difficult to culture cells with high reproducibility without damaging the cells.

In order to solve these problems, a method for producing cultured mucous membranes/skins by inoculating and culturing fibroblasts, keratinocytes, or the like by arranging collagen which is cross-linked in a gel or sponge form on a culture substrate is disclosed (Patent Document 1); however, many of the collagen types which are used are collagens which are solubilized and extracted from the connective tissues of cows or pigs and, due to the recent problems such as bovine spongiform encephalopathy (BSE) or foot and mouth disease, the use of the above is becoming more problematic in cases where medical applications are considered.

For the subculture operation, in the techniques in the related art, in order to culture adherent cells which divide repeatedly, a method in which, every time the proliferation reaches a target cell concentration after culturing the cells in a culture container for an appropriate period of time, an operation of separating cells from a culture surface and transferring some of the cells into a new culture container is continuously performed, is typical (for example, Patent Documents 2 and 3). Patent Document 2 discloses a method of carrying out culturing in a closed system while using a culture container which has a plurality of culture surfaces with different areas, starting cell culturing from the smallest culture surface area, and then separating cells with a scraper as the proliferation progresses, and gradually moving the cells to a larger culture surface area. In addition, a subculture operation in which the cell concentration is adjusted by connecting cell bags made of a resin with gas permeability and then mixing a culture solution in the bags is disclosed (Patent Document 3). However, in any of the methods, since the subculture operation involves extremely complicated work such as frequent solution exchanges, or an operation of peeling off the cells attached to the substrate and transferring these cells to a new culture container is performed, there are potentially many problems whereby the cells might be damaged and the proliferated form thereof destroyed.

Here, with regard to the substrate surface properties on which cells are cultured and the proliferative characteristics, the results of evaluating the relationship between the proliferated form of the cells and the water contact angle of the substrate are disclosed (Non-Patent Document 1) using an example in which L cells (secretory gastrointestinal cells) were cultured. The above results illustrate that, for substrates of which the water contact angle is in the range of 43° to 116°, when the cell density one hour after starting culturing was measured, the density of the cells which used a substrate of which the water contact angle was in the range of 60° to 70° was high and the adhesion of the cells was favorable regardless of the type of the substrate.

In addition, culturing techniques using the substrates in which convex-concave structure is formed on the surface of the substrate that cells are in contact with have recently been proposed (for example, Patent Documents 4 and 5). In many cases, culturing which uses a substrate provided with a convex-concave structure is spheroid culturing and the cells exhibit an aspect of proliferating in an aggregated form. However, the material of the substrate provided with a convex-concave structure is a cell adhesion material known in the related art such as cyclic olefin polymer (Patent Document 4), polydimethylsiloxane (Patent Document 5), or the like and, in spheroid culturing using the convex-concave structure on the substrate, even if the area that cells are in contact with the substrate is small, the form of the adhesion substantially does not change and cells form an anchorage. Hereby, there is a potential problem in that, when separating the cultured cells from the substrate, the cells maybe damaged and the proliferated form thereof destroyed.

Furthermore, while reports have been made regarding the effective shape and size of the convex-concave structure when the cells form the anchorage in cell culturing which uses a substrate provided with a convex-concave structure, there has been no description of the relationship between the water contact angle of a substrate surface and the adhesive characteristics or the proliferative characteristics.

RELATED DOCUMENT

Patent Document

[Patent Document 1] Japanese Unexamined Patent Publication No. 2004-147585
[Patent Document 2] Japanese Unexamined Patent Publication No. 2004-129558
[Patent Document 3] Japanese Unexamined Patent Publication No. H07-047105 [Patent Document 4] Japanese Published Patent Application A-2007-097121
[Patent Document 5] Japanese Unexamined Patent Publication No. 2010-88347

Non-patent Document

[Non-Patent Document 1] Y. Tamada, Y. Ikeda, Journal of Colloid and Interface Science 155, 334-339 (1993)

SUMMARY OF THE INVENTION

The present invention has an object of providing medical instrument which is able to separate cells in contact with or hold on a surface of a substrate from the substrate without damaging the cells.

In addition, the present invention has an object of providing cultured cells able to maintain a drug metabolizing system enzyme activity over a long period. Since it may be considered that it is possible to favorably develop cultured cells which are able to maintain drug metabolizing system enzyme activity for regenerative medicine or the like, the significance of the present invention is extremely great.

The present invention is shown below.

(1) Medical instrument including a substrate, in which cells are in contact with or held on a surface of the substrate, and at least the surface of the substrate which holds the cells is formed of a fluorine-containing cyclic olefin polymer which contains a repeating structure unit represented by Formula (1),

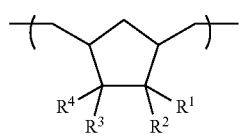

(1)

wherein in Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine, $R^1$ to $R^4$ are selected from hydrogen, an alkyl with 1 to 10 carbon atoms, an alkoxy with 1 to 10 carbon atoms, or an alkoxyalkyl with 2 to 10 carbon atoms in a case where $R^1$ to $R^4$ are groups which do not contain fluorine, $R^1$ to $R^4$ may be the same as or different from each other, and $R^1$ to $R^4$ may be bonded to each other to form a cyclic structure.

(2) The medical instrument according to (1), in which a water contact angle of the surface which is in contact with or holds cells is equal to or more than 70° and equal to or less than 160°.

(3) The medical instrument according to (1) or (2), in which the water contact angle of the surface which is in contact with or holds cells is equal to or more than 70° and equal to or less than 120°.

(4) The medical instrument according to (1), in which at least the surface of the substrate which is in contact with cells is provided with a convex-concave structure.

(5) The medical instrument according to (4), in which a water contact angle of the surface which is in contact with cells is equal to or more than 121° and equal to or less than 160°.

(6) The medical instrument according to any one of (1) to (5), in which at least the surface of the substrate which is in contact with or holds cells is formed of a fluorine-containing cyclic olefin polymer composition which includes the fluorine-containing cyclic olefin polymer, a photocurable compound, and a photo-curing initiator.

(7) The medical instrument according to (6), in which a mass ratio of the fluorine-containing cyclic olefin polymer and the photocurable compound (fluorine-containing cyclic olefin polymer/photocurable compound) in the fluorine-containing cyclic olefin polymer composition is 99.9/0.1 to 50/50.

(8) The medical instrument according to any one of (1) to (7), which is used for culturing cells which are in contact with or held on a surface of the substrate.

(9) The medical instrument according to (8), in which cells proliferate as forming a colony in a cell culture.

(10) The medical instrument according to (8) or (9), in which the cultured cells are floated by using a buffer solution and then separated from the surface.

(11) A method for culturing cells including a step of inoculating cells over the surface of the substrate of the medical instrument according to any one of (1) to (10) so as to be in contact with or held on the surface; a step of obtaining cultured cells by culturing the cells; and a step of floating the cultured cells from the surface by adding a buffer solution over the surface.

(12) A fluorine-containing cyclic olefin polymer which, in medical instrument which is provided with a substrate and in which cells are in contact with or held on a surface of the substrate, forms at least the surface of the substrate which holds cells, the fluorine-containing cyclic olefin polymer including a repeating structure unit represented by Formula (1),

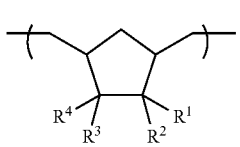

(1)

wherein in Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine, $R^1$ to $R^4$ are selected from hydrogen, an alkyl with 1 to 10 carbon atoms, an alkoxy with 1 to 10 carbon atoms, or an alkoxyalkyl with 2 to 10 carbon atoms in a case where $R^1$ to $R^4$ are groups which do not contain fluorine, $R^1$ to $R^4$ may be the same as or different from each other, and $R^1$ to $R^4$ may be bonded to each other to form a cyclic structure.

(13) A fluorine-containing cyclic olefin polymer composition which, in medical instrument which is provided with a substrate and in which cells are in contact with or held on a surface of the substrate, forms at least the surface of the substrate which holds cells, the fluorine-containing cyclic olefin polymer composition including a fluorine-containing cyclic olefin polymer which contains a repeating structure unit represented by Formula (1) below; a photocurable compound; and a photo-curing initiator,

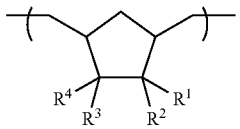

wherein in Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine, $R^1$ to $R^4$ are selected from hydrogen, alkyl with 1 to 10 carbon atoms, alkoxy with 1 to 10 carbon atoms, or alkoxyalkyl with 2 to 10 carbon atoms in a case where $R^1$ to $R^4$ are groups which do not contain fluorine, $R^1$ to $R^4$ may be the same as or different from each other, and $R^1$ to $R^4$ may be bonded to each other to form a cyclic structure.

(14) Cultured cells which maintain drug metabolizing system enzyme activity for at least 7 days.

It is possible to provide medical instrument which is able to separate cells which are in contact with or held on a surface of a substrate from the substrate without damaging the cells.

BRIEF DESCRIPTION OF THE DRAWINGS

The object described above and other objects, features, and advantages will be made clearer from favorable embodiments which will be described below and the accompanying diagrams below.

DESCRIPTION OF EMBODIMENTS

Figure 1:
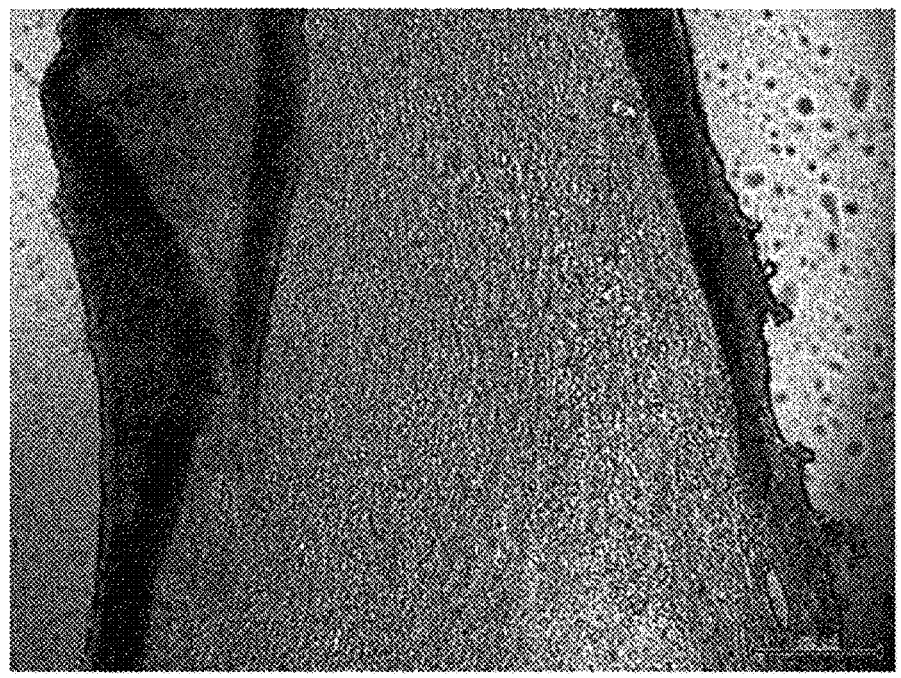
FIG. 1 is mouse embryo fibroblasts dipped in phosphate buffered physiological saline and floated in sheet form.

Description will be given below of embodiments using diagrams. Here, the same reference numerals are given to the same constituent elements in all the diagrams, and description thereof will not be repeated.

The medical instrument according to the present embodiment is medical instrument provided with a substrate, in which cells are in contact with or held on a surface of the substrate. In addition, at least a surface of the substrate described above on which the cells are held is formed of a fluorine-containing cyclic olefin polymer which contains a repeating structure unit represented by Formula (1).

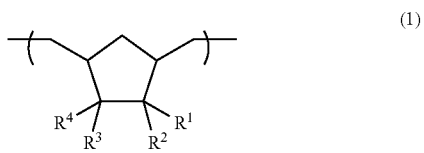

In Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine. $R^1$ to $R^4$ are selected from hydrogen, an alkyl with 1 to 10 carbon atoms, an alkoxy with 1 to 10 carbon atoms, or an alkoxyalkyl with 2 to 10 carbon atoms in a case where $R^1$ to $R^4$ are groups which do not contain fluorine. $R^1$ to $R^4$ may be the same as or different from each other. $R^1$ to $R^4$ may be bonded to each other to form a cyclic structure.

Here, the substituent groups such as alkyl, alkoxy, and alkoxyalkyl maybe described as an alkyl group, an alkoxy group, and an alkoxyalkyl group respectively in the present specification.

In addition, it is also possible for a "repeating structure unit" in the present specification to be simply expressed as a "structure unit".

The present inventors have newly discovered that, in a case of forming a surface of a substrate which configures medical instrument on which cells are in contact or held using a fluorine-containing cyclic olefin polymer which contains a repeating structure unit represented by Formula (1) described above or a composition which includes the fluorine-containing cyclic olefin polymer, it is possible to easily float the cells which are held on the surface, for example, using a buffer solution such as phosphate buffered physiological saline. Accordingly, with the medical instrument described above according to the present embodiment, it is possible to separate the cells which are in contact with or held on a surface of a substrate from the substrate without damaging the cells by floating the cells using a buffer solution.

Detailed description will be given below of the medical instrument according to the present embodiment.

The medical instrument according to the present embodiment is provided with a substrate and is used in a form in which cells and/or a culture solution is in contact with or held on a surface of the substrate. The medical instrument is used, for example, in order to culture cells which are in contact with or held on a surface of a substrate or to perform an inspection using cells which are in contact with or held on a surface of a substrate. In the present embodiment, it is possible to include a culture bag, a culture plate, a culture petri dish, a culture dish, a culture flask, a culture tube, and the like as an example of the medical instrument described above. In medical instrument for culturing cells, it is possible to make the surface described above the culturing surface for culturing the cells.

In the medical instrument according to the present embodiment, at least a surface on which cells of a substrate are in contact or held is formed of a fluorine-containing cyclic olefin polymer which contains a repeating structure unit represented by Formula (1) described above. Hereby, as described above, medical instrument is obtained which is able to float cells which are held on a surface of a substrate or cells which are cultured over a surface from the substrate using a buffer solution. For this reason, it is possible to separate cells which are in contact with or held on a surface of a substrate from the substrate without damaging the cells.

Here, it is possible to float cells from the substrate in a case of adding a certain type of buffer solution over a surface of the substrate, for example, phosphate buffered physiological saline, a case of dipping the substrate in a phosphate buffered physiological saline, or the like.

In addition, by forming at least a surface of a substrate, on which cells are in contact or held, of a fluorine-containing cyclic olefin polymer which contains a repeating structure unit represented by Formula (1) described above, it is possible to realize a substrate in which, while the cells which are held on the surface form an appropriate anchorage with respect to the substrate, the cells are not strongly adhered or attached to the surface. Hereby, in cell culturing, it is possible to be proliferated the cells while forming a colony in the thickness direction.

Here, regarding the form of the cells which proliferate while forming a colony in a thickness direction, it is possible to observe the cultured cells using, for example, a bright and dark visual field microscope, a phase contrast microscope, a fluorescence microscope, or the like. In particular, a favorable method for observing the form of the cells is fluorescence microscope observation of fluorescent colors which are dyed with fluorescence emission reagents, in which each part of the cell nucleus of a cell, the cytoskeleton protein, and the like separately.

In medical instrument which is used in order to culture normal cells, since the proliferated cells proliferate while adhered or attached to a culture surface, the cells proliferate in a planar state against the thickness direction. In this case, since there is no longer an anchorage to which the cells are adhered or attached when the cells cover the culture surface, proliferation is prevented due to the influence of contact inhibition or the like. On the other hand, it is possible to consider using a subculture operation which carries out culturing by repeating inoculation in order to efficiently carry out the cell culturing; however, there is a concern in that cells will be damaged by work in which the cells are peeled off and transferred to a new culture container. In addition, the subculture operation involves extremely complicated work such as frequent solution exchanges.

In contrast to this, according to the present embodiment, for forming a surface of a substrate on which cells are held using a fluorine-containing cyclic olefin polymer of Formula (1) described above, it is possible to suppress the proliferated cells from being adhered or attached to the surface of the substrate. For this reason, even without a subculture operation, it is possible to proliferate the cells so as to form a colony in the thickness direction. Accordingly, it is possible to perform more effective cell culturing without damaging the cells and complicating the operation.

In addition, cultured cells which are produced using the medical instrument of the present embodiment maintain drug metabolizing system enzyme activity for at least 7 days. In other words, the cultured cells are cultured cells which are grown while maintaining substantially the same functions as cell proliferated in vivo and the selection of the type of cell is not limited. Alternatively, it is possible to culture living cells normally except for extremely limited types of cell such as viruses or bacteria with a high possibility of causing gene mutation. The drug metabolizing system enzyme activity of the cell is maintained for at least 7 days without being stored at low temperatures or being subjected to a special culture storage operation (for example, storing with an excessive amount of oxygen or the like) and cultured cells which maintain the drug metabolizing system enzyme activity for 10 days are preferable. Cultured cells which maintain the drug metabolizing system enzyme activity for 14 days are particularly preferable. On the other hand, the shape of the cell does not particularly need to be limited; however, examples thereof include sheet-shaped cells, colony-forming (including spheroid) cells, nervous system type cells, and the like. In particular, in the field of regenerative medicine, it is desired to keep the drug metabolizing system enzyme activity in a short period as well as biological cells and it is important to enable favorable production, as in the cultured cells in the present embodiment.

In addition, the cultured cells of the present embodiment are expected to maintain the same functions over a long period even in drug development, biological chemicals, and cosmetics and the present invention could be used in the worldwide stream.

In addition, it is possible to improve the formability of the substrate by using the fluorine-containing cyclic olefin polymer described above, and make a new medical instrument having an industrial value.

Forming the substrate of the fluorine-containing cyclic olefin polymer which cells are in contact with or held on at least a surface of it includes, for example, a case where a substrate is formed of a film (also referred to as a cultured cell sheet), which is formed of the fluorine-containing cyclic olefin polymer described above, being attached over a surface of a support body made of another material, a case where a substrate is formed of a coated film, which is formed of the fluorine-containing cyclic olefin polymer described above, being formed by being applied over a surface of a support body formed of other material and dried, and a case where the entirety of the substrate is formed of a mold with the fluorine-containing cyclic olefin polymer described above.

In addition, the cultured cells in a laminated body, which are produced on the medical instrument of the present embodiment, that are covered and laminated with cotton, fabric, non-woven fabric, or the like, may be provided. Alternatively, a moisturizer such as glycerine may be impregnated into this laminated body. In other words, it is also possible to use the cultured cells which are produced by the medical instrument of the present embodiment for medical practices as peeling a cover off such as a laminated body described above, directly attaching this to an affected part as an application for regenerative medicine, and subsequently removing the film.

As the medical instrument, a water contact angle of a surface which is in contact with or holds cells is, for example, equal to or more than 70° and equal to or less than 160°. Hereby, it is possible to suppress the adhesion or attachment of cells onto a substrate which is caused through a family of proteins (adhesion molecules or proteins) such as vitronectin or fibronectin and the like which is present in the extracellular matrix of a culture solution. Hereby, by using the cell culture substrate of which the appropriately small compatibility between cells and a culture solution as extracellular matrix which is water as a main component and it, it is possible to more easily float the cells proliferated on the such surface as suppressing adhesion and attachment, for example, by using a buffer solution such as phosphate buffered physiological saline. For this reason, when separating cells from a substrate, it is possible to more reliably suppress damage to the cells. In addition, in the process of proliferating cells, it is easier to be proliferated cells so as to form a colony in the thickness direction and more effective cell culturing is possible. In other words, by culturing cells with medical instrument made of a substrate that the water contact angle is adjusted within the range described above, it is possible to be proliferated cells in forming a colony of cells, suppressing attachment or adhesion of the cells to the culture instrument and preserving the interaction of each interface of a substrate surface, cells, and a culture solution. From the point of view of suppressing damage to cells or the point of view of performing effective cell culturing, the water contact angle described above is more preferably equal to or more than 75° and equal to or less than 155° and particularly preferably equal to or more than 80° and equal to or less than 150°.

Regarding the water contact angle of a surface of a substrate, in one aspect, the substrate is preferably used when the water contact angle of the substrate surface is equal to or more than 70° and equal to or less than 120° and it is possible to control the water contact angle by appropriately selecting the material which forms the surface of the substrate or various conditions in the method for producing the substrate. From the point of view of suppressing damage to cells or the point of view of performing effective cell culturing, the water contact angle described above is more preferably equal to or more than 75° and equal to or less than 115° and particularly preferably equal to or more than 80° and equal to or less than 110°.

In addition, in another aspect, it is also possible to make the water contact angle higher and, for example, it is also possible to set the water contact angle of a surface of the substrate to be within the range of 121° to 160°. In order to realize a water contact angle of 121° to 160° in this described matter above, a control method forming a convex-concave structure on a surface of a substrate is preferably used. From the point of view of suppressing damage to cells or the point of view of performing effective cell culturing, the water contact angle described above is more preferably equal to or more than 123° and equal to or less than 155° and particularly preferably equal to or more than 125° and equal to or less than 150°. In the present embodiment, forming the surface of the substrate described above using the fluorine-containing cyclic olefin polymer which contains a repeating structure unit represented by Formula (1) described above is one of the important elements for setting the water contact angle to be in a desired range.

It is possible to measure the water contact angle on the basis of Japanese Industrial Standard JIS-R 3257 (methods for testing the wettability of a substrate glass surface) using a method of dripping water droplets with a capacity of 4 μl or less, in which the shape of the water droplet is able to be seen as a spherical shape under constant temperature and constant humidity conditions of 25±5° C. and 50±10%, onto a substrate surface and measuring the angle of the contact interface between the substrate and the water droplets within one minute after the water droplets come into contact with the substrate surface according to a sessile drop method. In the present embodiment, for example, it is possible to treat the numeric value within one minute directly after the water droplets come into contact in the method described above as the physical property value in the same manner as the numeric value which is used for the physical property value of various types of plastic material.

Examples of the types of cells regardless of whether floating cells or adherent cells in the case of animal cells which are able to be treated in the medical instrument according to the present embodiment include fibroblasts, mesenchymal stem cells, hematopoietic stem cells, neural stem cells, nerve cells, corneal epithelial cells, mouth mucosa cells, retinal pigment cells, periodontal membrane stem cells, myofibroblasts, cardiac muscle cells, liver cells, pancreatic endocrine cells, dermal keratinocytes, dermal fibroblasts, precursor cells derived from subcutaneous fat, kidney cells, bottom hair root sheath cells, nasal mucous membrane epithelial cells, mesenchymal stem cells, vascular endothelium precursor cells, vascular endothelium cells, vascular smooth muscle cells, osteoblastic cells, cartilage cells, skeletal muscle cells, immortalized cells, cancer cells, keratinocytes, embryonic stem cells (ES cells), EBV phenotypic transformation B cells, induced pluripotent stem cells (iPS cells), and the like and more specific examples thereof include HeLa cells, CHO cells, Cos cells, HL-60 cells, Hs-68 cells, MCF7 cells, Jurkat cells, Vero cells, PC-12 cells, K562 cells, L cells, 293 cells, HepG2 cells, U-937 cells, Caco-2 cells, HT-29 cells, A549 cells, B16 cells, MDCK cells, BALB/3T3 cells, V79 cells, 3T3-L1 cells, NIH/3T3 cells, Raji cells, NSCLC cells, A431 cells, Sf9 cells, SH-SY5Y cells, BHK-21 cells, J774 cells, C2C12 cells, 3T3-Swiss albino cells, MOLT-4 cells, CV-1 cells, F9 cells, MC3T3-E1 cells, HaCaT cells, L5178Y cells, HuH-7 cells, Rat1 cells, Saos-2 cells, TIG cells, CHL cells, WI-38 cells, MRC-5 cells, Hep3B cells, SK-N-SH cells, MIN6 cells, KATO cells, C3H/10T1/2 cells, DT40 cells, PLC/PRF/5 cells, IMR-90 cells, FM3A cells, and the like. In addition, the cells may be either primary cells or subcultured cells.

Examples of derivations of these cells include cells of various types of living beings such as humans, dogs, rats, mice, birds, pigs, cows, and insects or tissues which are formed by aggregating the above, organs, microorganisms, viruses, and the like, and more specific examples thereof include human cervical cancer derivations, Chinese hamster ovary derivations, CV-1 cell derivations, human myelocytic leukemia derivations, human breast cancer derivations, human T cell leukemia derivations, Africa green monkey kidney derivations, human adrenal gland pith pheochromocytomas derivations, human myelocytic leukemia derivations, C3H mouse epithelial tissue derivations, human embryonal kidney derivations, human hepatic cancer derivations, human histiocytic leukemia derivations, human colorectal cancer derivations, human lung cancer derivations, mouse melanoma derivations, dog kidney derivations, Balb/c mouse fetus derivations, Chinese hamster lung derivations, Swiss 3T3 derivations, NIH Swiss mouse fetus derivations, human Burkitt lymphoma derivations, human lung non-small cell cancer derivations, human skin Epidermoid Carcinoid derivations, moth larva ovary derivations, human neuroblast tumor derivations, Sirian golden hamster kidney derivations, mouse macrophage derivations, mouse muscular tissue derivations, inferior Swiss mouse fetus derivations, human acute T cell leukemia derivations, mouse EC cell OTT6050 derivations, mouse calvaria derivations, human epidermal keratinocyte derivations, DBA/2 mouse thymic tumor derivations, human stem cell cancer derivations, rat fibroblast derivations, human myelogenous osteosarcoma derivations, human fetal lung derivations, human fetal lung derivations, human neuroblast tumor derivations, mouse insulinoma derivations, human gastric cancer derivations, C3H mouse fetus derivations, chicken B cell leukemia derivations, mouse spontaneous mammary tumor derivations, and the like.

Next, detailed description will be given of a fluorine-containing cyclic olefin polymer.
(Fluorine-Containing Cyclic Olefin Polymer)

As described above, the fluorine-containing cyclic olefin polymer contains a repeating structure unit represented by Formula (1). In the present embodiment, it is possible to form at least a surface of the substrate of the medical instrument in which cells are in contact with or held on a surface of a substrate using the fluorine-containing cyclic olefin polymer.

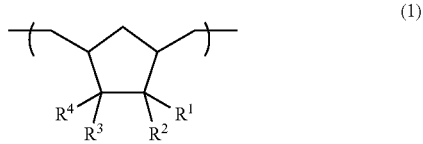

(1)

(In Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine. $R^1$ to $R^4$ are selected from hydrogen, an alkyl with 1 to 10 carbon atoms, an alkoxy with 1 to 10 carbon atoms, or an alkoxyalkyl with 2 to 10 carbon atoms in a case where $R^1$ to $R^4$ are groups which do not contain fluorine. $R^1$ to $R^4$ may be the same as or different from each other. $R^1$ to $R^4$ may be bonded to each other to form a cyclic structure.)

Examples of $R^1$ to $R^4$ in Formula (1) include fluorine; an alkyl with 1 to 10 carbon atoms which contains fluorine such as an alkyl in which some or all of hydrogen atoms of an alkyl group are substituted with fluorine such as fluoromethyl, difluoromethyl, trifluoromethyl, trifluoroethyl, pentafluoroethyl, heptafluoropropyl, hexafluoroisopropyl, heptafluoroisopropyl, hexafluoro-2-methylisopropyl, perfluoro-2-methylisopropyl, n-perfluorobutyl, n-perfluoropentyl, and perfluorocyclopentyl; an alkoxy with 1 to 10 carbon atoms which contains fluorine such as an alkoxy in which some or all of hydrogen atoms of an alkoxy are substituted with fluorine such as fluoromethoxy, difluoromethoxy, trifluoromethoxy, trifluoroethoxy, pentafluoroethoxy, heptafluoropropoxy, hexafluoroisopropoxy, heptafluoroisopropoxy, hexafluoro-2-methylisopropoxy, perfluoro-2-methylisopropoxy, n-perfluorobutoxy, n-perfluoropentoxy, and perfluorocyclooentoxy; or an alkoxyalkyl with 2 to 10 carbon atoms which contains fluorine such as an alkoxyalkyl in which some or all of hydrogen atoms of an alkoxyalkyl are substituted with fluorine such as fluoromethoxymethyl, difluoromethoxymethyl, trifluoromethoxymethyl, trifluoroethoxymethyl, pentafluoroethoxymethyl, heptafluoropropoxymethyl, hexafluoroisopropoxymethyl, heptafluoroisopropoxymethyl, hexafluoro-2-methylisopropoxymethyl, perfluoro-2-methylisooropoxvmethvl, n-perfluorobutoxymethyl, n-perfluoropentoxymethyl, and perfluorocyclopentoxymethyl.

In addition, $R^1$ to $R^4$ may be bonded to each other to form a cyclic structure and may form a ring such as perfluorocycloalkyl and perfluorocycloether via oxygen.

Furthermore, examples of other $R^1$ to $R^4$ which do not contain fluorine include hydrogen; an alkyl with 1 to 10 carbon atoms such as methyl, ethyl, propyl, isopropyl, 2-methylisopropyl, n-butyl, n-pentyl, and cyclopentyl; an alkoxy with 1 to 10 carbon atoms such as methoxy, ethoxy, propoxy, butoxy, and pentoxy; or an alkoxyalkyl with 2 to 10 carbon atoms such as methoxymethyl, ethoxymethyl, propoxymethyl, butoxymethyl, and pentoxymethyl.

The fluorine-containing cyclic olefin polymer may only have a structure unit represented by Formula (1) or may have another structure unit along with the structure unit represented by Formula (1). In addition, the fluorine-containing cyclic olefin polymer may include two or more types of structure units which are structure units represented by Formula (1) and in which at least one of $R^1$ to $R^4$ is different from each other.

Specific examples of the fluorine-containing cyclic olefin polymer which contains a repeating structure unit represented by Formula (1) include poly(1-fluoro-2-trifluoromethyl-3,5-cyclopentylene ethylene), poly(1-fluoro-1-trifluoromethyl-3,5-cyclopentylene ethylene), poly(1-methyl-1-fluoro-2-trifluoromethyl-3,5-cyclopentylene ethylene), poly(1,1-difluoro-2-trifluoromethyl-3,5-cyclopentylene ethylene), poly(1,2-difluoro-2-trifluoromethyl-3,5-cyclopentylene ethylene), poly(1-perfluoroethyl-3,5-cyclopentylene ethylene), poly(1,1-bis(trifluoromethyl)-3,5-cyclopentylene ethylene), poly(1,1,2-trifluoro-2-trifluoromethyl-3,5-cyclopentylene ethylene), poly(1,2-bis(trifluoromethyl)-3,5-cyclopentylene ethylene), poly(1-perfluoropropyl-3,5-cyclopentylene ethylene), poly(1-methyl-2-perfluoropropyl-3,5-cyclopentylene ethylene), poly(1-butyl-2-perfluoropropyl-3,5-cyclopentylene ethylene), poly(1-perfluoro-iso-propyl-3,5-cyclopentylene ethylene), poly(1-methyl-2-perfluoro-iso-propyl-3,5-cyclopentylene ethylene), poly(1,2-difluoro-1,2-bis(trifluoromethyl)-3,5-cyclopentylene ethylene), poly(1,1,2,2,3,3,3a,6a-octafluorocyclopentyl-4,6-cyclopentylene ethylene), poly(1,1,2,2,3,3,4,4,3a,7a-decafluorocyclohexyl-5,7-cyclopentylene ethylene), poly(1-perfluorobutyl-3,5-cyclopentylene ethylene), poly(1-perfluoro-iso-butyl-3,5-cyclopentylene ethylene), poly(1-perfluoro-tert-butyl-3,5-cyclopentylene ethylene), poly(1-methyl-2-perfluoro-iso-butyl-3,5-cyclopentylene ethylene), poly(1-butyl-2-perfluoro-iso-butyl-3,5-cyclopentylene ethylene), poly(1,2-difluoro-1-trifluoromethyl-2-perfluoroethyl-3,5-cyclopentylene ethylene),
poly(1-(1-trifluoromethyl-2,2,3,3,4,4,5,5-octafluoro-cyclopentyl)-3,5-cyclopentylene ethylene)),
poly((1,1,2-trifluoro-2-perfluorobutyl)-3,5-cyclopentylene ethylene),
poly(1,2-difluoro-1-trifluoromethyl-2-perfluorobutyl-3,5-cyclopentylene ethylene),
poly(1-fluoro-1-perfluoroethyl-2,2-bis(trifluoromethyl)-3,5-cyclopentylene ethylene),
poly(1,2-difluoro-1-perfluoropropanyl-2-trifluoromethyl-3,5-cyclopentylene ethylene), poly(1-perfluorohexyl-3,5-cyclopentylene ethylene), poly(1-methyl-2-perfluorohexyl-3,5-cyclopentylene ethylene), poly(1-butyl-2-perfluorohexyl-3,5-cyclopentylene ethylene), poly(1-hexyl-2-perfluorohexyl-3,5-cyclopentylene ethylene), poly(1-octyl-2-perfluorohexyl-3,5-cyclopentylene ethylene), poly(1-perfluoroheptyl-3,5-cyclopentylene ethylene), poly(1-perfluorooctyl-3,5-cyclopentylene ethylene), poly(1-perfluorodecanyl-3,5-cyclopentylene ethylene), poly(1,1,2-trifluoro-perfluoropentyl-3,5-cyclopentylene ethylene), poly(1,2-difluoro-1-trifluoromethyl-2-perfluorobutyl-3,5-cyclopentylene ethylene),
poly(1,1,2-trifluoro-perfluorohexyl-3,5-cyclopentylene ethylene), poly(1,2-difluoro-1-trifluoromethyl-2-perfluoropentyl-3,5-cyclopentylene ethylene),
poly(1,2-bis(perfluorobutyl)-3,5-cyclopentylene ethylene), poly(1,2-bis(perfluorohexyl)-3,5-cyclopentylene ethylene), poly(1-methoxy-2-trifluoromethyl-3,5-cyclopentylene ethylene), poly(1-tert-butoxymethyl-2-trifluoromethyl-3,5-cyclopentylene ethylene),
poly(1,1,3,3,3a,6a-hexafluorofuranyl-3,5-cyclopentylene ethylene), poly(1-fluoro-2-trifluoromethoxy-3,5-cyclopentylene ethylene), poly(1-fluoro-1-trifluoromethoxy-3,5-cyclopentylene ethylene), poly(1-methyl-1-fluoro-2-trifluoromethoxy-3,5-cyclopentylene ethylene), poly(1,1-difluoro-2-trifluoromethoxy-3,5-cyclopentylene ethylene), poly(1,2-difluoro-2-trifluoromethoxy-3,5-cyclopentylene ethylene), poly(1-perfluoroethoxy-3,5-cyclopentylene ethylene), poly(1,1-bis(trifluoromethoxy)-3,5-cyclopentylene ethylene), poly(1,1,2-trifluoro-2-trifluoromethoxy-3,5-cyclopentylene ethylene), poly(1,2-bis(trifluoromethoxy)-3,5-cyclopentylene ethylene), poly(1-perfluoropropoxy-3,5-cyclopentylene ethylene), poly(1-methyl-2-perfluoropropoxy-3,5-cyclopentylene ethylene), poly(1-butyl-2-perfluoropropoxy-3,5-cyclopentylene ethylene), poly(1-perfluoro-iso-propoxy-3,5-cyclopentylene ethylene), poly(1-methyl-2-perfluoro-iso-propoxy-3,5-cyclopentylene ethylene),
poly(1,2-difluoro-1,2-bis(trifluoromethoxy)-3,5-cyclopentylene ethylene), poly(1-perfluorobutoxy-3,5-cyclopentylene ethylene), poly(1-perfluoro-iso-butoxy-3,5-cyclopentylene ethylene), poly(1-perfluoro-tert-butoxy-3,5-cyclopentylene ethylene), poly(1-methyl-2-perfluoro-iso-butoxy-3,5-cyclopentylene ethylene), poly(1-butyl-2-perfluoro-iso-butoxy-3,5-cyclopentylene ethylene), poly(1,2-difluoro-1-trifluoromethoxy-2-perfluoroethoxy-3,5-cyclopentylene ethylene),
poly(1,1,2-trifluoro-2-perfluorobutoxy-3,5-cyclopentylene ethylene),
poly(1,2-difluoro-1-trifluoromethoxy-2-perfluorobutoxy-3,5-cyclopentylene ethylene),
poly(1-fluoro-1-perfluoroethoxy-2,2-bis(trifluoromethoxy)-3,5-cyclopentylene ethylene),
poly(1,2-difluoro-1-perfluoropropoxy-2-trifluoromethoxy-3,5-cyclopentylene ethylene), poly(1-perfluorohetoxy-3,5-cyclopentylene ethylene), poly(1-methyl-2-perfluorohetoxy-3,5-cyclopentylene ethylene), poly(1-butyl-2-perfluorohetoxy-3,5-cyclopentylene ethylene), poly(1-hexyl-2-perfluorohetoxy-3,5-cyclopentylene ethylene), poly(1-octyl-2-perfluorohetoxy-3,5-cyclopentylene ethylene), poly(1-perfluoroheptoxy-3,5-cyclopentylene ethylene), poly(1-perfluorooctoxy-3,5-cyclopentylene ethylene), poly(1-perfluorodetoxy-3,5-cyclopentylene ethylene), poly(1,1,2-trifluoro-perfluoropentoxy-3,5-cyclopentylene ethylene),
poly(1,2-difluoro-1-trifluoromethoxy-2-perfluorobutoxy-3,5-cyclopentylene ethylene),
poly(1,1,2-trifluoro-2-perfluorohetoxy-3,5-cyclopentylene ethylene),
poly(1,2-difluoro-1-trifluoromethoxy-2-perfluoropentyl-3,5-cyclo pentylene ethylene),
poly(1,2-bis(perfluorobutoxy)-3,5-cyclopentylene ethylene), poly(1,2-bis(perfluorohetoxy)-3,5-cyclopentylene ethylene), poly(1-methoxy-2-trifluoromethoxy-3,5-cyclopentylene ethylene), poly(1-tert-butoxymethyl-2-trifluoromethoxy-3,5-cyclopentylene ethylene), poly(1-(2',2',2'-trifluoroethoxy)-3,5-cyclopentylene ethylene),
poly(1-(2',2',3',3',3'-pentafluoropropoxy)-3,5-cyclopentylene ethylene),
poly(1-methyl-2-(2',2',3',3',3'-pentafluoropropoxy)-3,5-cyclopentylene ethylene),
poly(1-butyl-2-(2',2',3',3',3'-pentafluoropropoxy)-3,5-cyclopentylene ethylene),
poly(1-(1',1',1'-trifluoro-iso-propoxy)-3,5-cyclopentylene ethylene),
poly(1-methyl-(1',1',1'-trifluoro-iso-propoxy)-3,5-cyclopentylene ethylene),
poly(1-(2',2',3',3',4',4',4'-heptafluorobutoxy)-3,5-cyclopentylene ethylene),
poly(1-(1',1',1'-trifluoro-iso-butoxy)-3,5-cyclopentylene ethylene),
poly(1-(1',1',1'-trifluoro-iso-butoxy)-3,5-cyclopentylene ethylene), poly(1-methyl-2-(1',1',1'-trifluoro-iso-butoxy)-3,5-cyclopentylene ethylene),
poly(1-butyl-2-(1',1',1'-trifluoro-iso-butoxy)-3,5-cyclopentylen e ethylene),
poly(1,2-difluoro-1-trifluoromethoxy-2-(2',2',2'-trifluoroethoxy)-3,5-cyclopentylene ethylene),
poly(1,1,2-trifluoro-2-(2',2',3',3',4',4',4'-heptafluorobutoxy)-3,5-cyclopentylene ethylene),
poly(1,2-difluoro-1-trifluoromethoxy-2-(2',2',3',3',4',4',4'-heptafluorobutoxy)-3,5-cyclopentylene ethylene),
poly(1-fluoro-1-(2',2',2'-trifluoroethoxy)-2,2-bis(trifluoromethoxy))-3,5-cyclopentylene ethylene),
poly(1,2-difluoro-1-(2',2',3',3',3'-pentafluoropropoxy)-2-trifluoromethoxy-3,5-cyclopentylene ethylene),
poly(1-(2',2',3',3',4',4',5',5',6',6'-undecafluorohetoxy)-3,5-cyclopentylene ethylene),
poly(1-methyl-2-(2',2',3',3',4',4',5',5',6',6'-undecafluorohetoxy)-3,5-cyclopentylene ethylene),
poly(1-butyl-2-(2',2',3',3',4',4',5',5',6',6'-undecafluorohetoxy)-3,5-cyclopentylene ethylene),
poly(1-hexyl-2-(2',2',3',3',4',4',5',5',6',6'-undecafluorohetoxy)-3,5-cyclopentylene ethylene),
poly(1-octyl-2-(2',2',3',3',4',4',5',5',6',6'-undecafluorohetoxy)-3,5-cyclopentylene ethylene),
poly(1-(2',2',3',3',4',4',5',5',6',6',7',7',7'-tridecafluoroheptoxy)-3,5-cyclopentylene ethylene),
poly(1-(2',2',3',3',4',4',5',5',6',6',7',7',8',8',8'-pentadecafluorooctoxy)-3,5-cyclopentylene ethylene),
poly(1-(2',2',3',3',4',4',5',5',6',6',7',7',8',8',9',9'-hepta decafluorodetoxy)-3,5-cyclopentylene ethylene),
poly(1,1,2-trifluoro-2-(1',1',1'-trifluoro-iso-propoxy)-3,5-cyclopentylene ethylene),
poly(1,2-difluoro-1-trifluoromethoxy-2-(2',2',3',3',4',4',4'-heptafluorobutoxy)-3,5-cyclopentylene ethylene),
poly(1,1,2-trifluoro-(2',2',3',3',4',4',5',5',6',6'-undecafluorohetoxy)-3,5-cyclopentylene ethylene),
poly(1,2-bis(2',2',3',3',4',4',4'-heptafluorobutoxy)-3,5-cyclopentylene ethylene),
poly(1,2-bis(2',2',3',3',4',4',5',5',6',6'-undecafluorohetoxy-3,5-cyclopentylene ethylene),
poly(1,2-difluoro-1-perfluoroethyl-2-trifluoromethyl-3,5-cyclopentylene ethylene),
poly(1,2-difluoro-1-perfluoro-iso-propyl-2-trifluoromethyl-3,5-cyclopentylene ethylene), and the like.

The molecular weight of the fluorine-containing cyclic olefin polymer is preferably 5,000 to 1,000,000 and more preferably 10,000 to 300,000, for example, in the weight average molecular weight (Mw) as a polystyrene converted value which is measured by a gel permeation chromatography (GPC) method at a sample concentration of 3.0 to 9.0 mg/ml. By setting the weight average molecular weight (Mw) to be the lower limit value described above or more, it is possible to more reliably obtain a mold in a favorable state where cracks or the like which are caused by external stress such as bending are not generated in a mold formed by a solution casting method or a mold applied to a substrate. In addition, by setting the weight average molecular weight (Mw) to be the upper limit value described above or less, it is possible to have a fluidity at which melt molding is easy.

Here, in the present specification, numeric value ranges indicated by "to" include the upper limit value thereof and the lower limit value.

In addition, the molecular weight distribution (Mw/Mn) which is a ratio of the weight average molecular weight (Mw) and the number average molecular weight (Mn) is preferably 1.3 to 5.0, more preferably 1.5 to 4.5, and particularly preferably 1.7 to 4.0. By setting the molecular weight distribution (Mw/Mn) to be the lower limit value described above or more, it is possible to improve the toughness of the films or molds which are produced by various types of molding methods such as a solution casting method or a melt molding method and more effectively suppress the generation of cracks or breaks caused by external stress. On the other hand, by setting the molecular weight distribution (Mw/Mn) to be the upper limit value described above or less, it is possible to suppress particularly low molecular weight components such as oligomers from eluting and to more reliably suppress the form of the cell proliferation of the present embodiment from being prevented by the water contact angle of the substrate surface being changed. By setting the weight average molecular weight (Mw) and the weight molecular distribution (Mw/Mn) to be in the ranges described above, it is possible to obtain particularly favorable medical instrument as used for cell culturing and inspection using the cells.

The glass transition temperature of the fluorine-containing cyclic olefin polymer according to differential scanning calorimetric analysis is preferably 50° C. to 300° C., more preferably 80° C. to 280° C., and even more preferably 100° C. to 250° C. When the glass transition temperature is within the ranges described above, it is possible to perform a heat sterilizing treatment, to maintain the shape under the usage environment and to more favorably obtain medical instrument as a substrate for cell culture and inspection using the cells, which has excellent fluidity with respect to a heating temperature in melt molding, has good production stability and is also excellent in hue.

The partially fluorinated polymer of Formula (1) of the present embodiment is different from the fully fluorinated polymers and has a large polarity due to the partially fluorinated polymer structure in which the main chain is a hydrocarbon and the side chain has a fluorine atom. From the reason, it can be dissolved well in polar solvents such as ethers and ketones which are generally commercially available solvents used at the time of polymer synthesis and also well in polar compounds such as a photocurable compound, and the mold exhibits excellent adhesion with respect to molds formed of generic resins such as PET and acrylic resin but has a hydrophobic surface property which is a feature as a fluorine based polymer.

Next, description will be given of a method for producing a fluorine-containing cyclic olefin polymer.

By using a film or mold which is formed by a fluorine-containing cyclic olefin polymer obtained by the production method described below as a substrate for cell culture and inspection using the cells, it is possible to favorably obtain medical instrument to which the cells of the present embodiment are hardly adhered or attached.

(Method for Producing Fluorine-Containing Cyclic Olefin Polymer)

In the present embodiment, it is possible to produce a fluorine-containing cyclic olefin polymer which is formed of a repeating structure unit substantially represented by Formula (1) by the method which will be described below. Hereby, it is possible to favorably obtain a fluorine-containing cyclic olefin polymer which is the raw material of a substrate for cell culture and inspection using the cells in which adhesion or attachment of the cells of the present embodiment is suppressed.

In detail, it is possible to synthesize a fluorine-containing cyclic olefin polymer by polymerizing a cyclic olefin monomer represented by Formula (2) below using a ring opening metathesis polymerization catalyst and hydrogenating the olefin portion in the main chain of the obtained polymer.

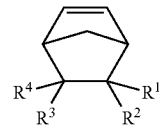

In Formula (2), $R^1$ to $R^4$ have the same meaning as in Formula (1) described above.

Here, a monomer other than the cyclic olefin monomer represented by Formula (2) may be included within a range which does not inhibit the effects of the present embodiment.

The fluorine-containing cyclic olefin polymer containing a structure unit represented by Formula (1) of the present embodiment is a fluorine-containing polymer in which a main chain double bond is hydrogenated after polymerizing the monomer represented by Formula (2) by ring-opening metathesis polymerization. A Schrock catalyst is preferably used for ring-opening metathesis polymerization but a Grubbs catalyst may also be used. Hereby, by using high polymerization catalytic activity for a polar monomer, it is possible to realize an industrially excellent production method. Here, these ring-opening metathesis polymerization catalysts may be used individually or may be used in a combination of two or more types. In addition, it is also possible to use a ring-opening metathesis polymerization catalyst which is formed by a combination of classical organic transition metal complexes, transition metal halogenated compositions, or transition metal oxides and Lewis acid as a co-catalyst.

In ring-opening metathesis polymerization of the cyclic olefin monomer, regarding the molar ratio between cyclic olefin monomer and ring-opening metathesis polymerization catalyst, in a case of a transition metal alkylidene catalyst such as tungsten, molybdenum, or ruthenium, the monomer is preferably 100 to 30,000 mol and more preferably 1,000 to 20,000 mol with respect to 1 mol of the transition metal alkylidene catalyst.

In addition, it is possible to use olefin or diene as a chain transfer agent in order to control the molecular weight and the distribution thereof in the described ranges above. Examples of olefins include α-olefins such as ethylene, propylene, 1-butene, 1-pentene, 1-hexene, and 1-octene or fluorine-containing olefins thereof and further include silicon-containing olefins such as vinyltrimethylsilane, allyltrimethylsilane, allyltriethylsilane, and allyltriisopropylsilane or fluorine- and silicon-containing olefins of the above. In addition, examples of dienes include non-conjugated diene such as 1,4-pentadiene, 1,5-hexadiene, and 1,6-heptadiene or fluorine-containing non-conjugated dienes thereof. These olefins, fluorine-containing olefins, or dienes may be each used individually or two or more types may be used together.

Regarding the usage amount of the chain transfer agent described above, the chain transfer agent is preferably 0.001 to 1, 000 mol with respect to 1 mol of the cyclic olefin monomer and more preferably 0.01 to 100 mol. In addition, the chain transfer agent is preferably 0.1 to 1,000 mol with respect to 1 mol of the transition metal alkylidene catalyst and more preferably 1 to 500 mol.

In addition, a solvent may not be used or a solvent may be used for ring-opening metathesis polymerization of the cyclic olefin monomer, and examples of particularly used solvents include ethers such as tetrahydrofuran, diethyl ether, dibutyl ether, dimethoxyethane, or dioxane, esters such as ethyl acetate, propyl acetate, or butyl acetate, aromatic hydrocarbons such as benzene, toluene, xylene, or ethyl benzene, aliphatic hydrocarbons such as pentane, hexane, or heptane, aliphatic cyclic hydrocarbons such as cyclopentane, cyclohexane, methyl cyclohexane, dimethyl cyclohexane, or decalin, halogenated hydrocarbons such as methylene dichloride, dichloroethane, dichloroethylene, tetrachloroethane, chlorobenzene, or trichlorobenzene, fluorine-containing aromatic hydrocarbons such as fluorobenzene, difluorobenzene, hexafluorobenzene, trifluoromethyl benzene, and metaxylene hexafluoride, fluorine-containing aliphatic hydrocarbons such as perfluorohexane, fluorine-containing aliphatic cyclic hydrocarbons such as perfluorocyclodecalin, or fluorine-containing ethers such as perfluoro-2-butyltetrahydrofuran. These may be used individually or may be used in a combination of two or more types.

In ring-opening metathesis polymerization of the cyclic olefin monomer, although there are differences depending on the reactivity of the monomer and the solubility to a polymerization solvent, the concentration of the cyclic olefin monomer with respect to the monomer solution is preferably 5 to 100 mass % and more preferably 10 to 60 mass %. In addition, the reaction temperature is preferably −30° C. to 150° C. and more preferably 30° C. to 100° C. In addition, the reaction time is preferably 10 minutes to 120 hours and more preferably 30 minutes to 48 hours. Furthermore, it is possible to stop the reaction using quenchers such as aldehydes such as butylaldehyde, ketones such as acetone, alcohols such as methanol, or water and to obtain a polymerization solution.

It is possible to obtain the cyclic olefin polymer of the present embodiment by a hydrogenating reaction on the olefin portion in the main chain of the polymer which is obtained by ring-opening metathesis polymerization of the cyclic olefin monomer using the catalyst. In addition, as long as the catalyst is able to hydrogenate the olefin portion in the main chain of the polymer without causing a hydrogenating reaction of the used solvent, the hydrogenating catalyst may be either a homogeneous metal complex catalyst or a heterogeneous metal carried catalyst. Examples of homogeneous metal complex catalysts include chlorotris(triphenylphosphine)rhodium, dichlorotris(triphenylphosphine) osmium, dichlorohydride bis(triphenylphosphine)iridium, dichlorotris(triphenylphosphine)ruthenium, dichlorotetrakis (triphenylphosphine)ruthenium, chlorohydride carbonyltris (triphenylphosphine)ruthenium, dichlorotris(trimethylphosphine)ruthenium, and the like and also examples of heterogeneous metal carried catalysts include palladium carried on activated carbon, palladium carried on alumina, rhodium carried on activated carbon, rhodium carried on alumina, ruthenium carried on activated carbon, ruthenium carried on alumina, and the like. These hydrogenating catalysts may be used individually and or can be used in a combination of two or more types. In particular, from the point of view of cell culturing, palladium carried on activated carbon or palladium carried on alumina which is able to be easily removed by filtration is favorably used.

When carrying out a hydrogenating treatment on the olefin portion in the main chain described above, regarding the usage amount of the hydrogenating catalyst in a case of using a homogeneous or heterogeneous hydrogenating catalyst, the metal components in the hydrogenating catalyst are preferably $5 \times 10^{-4}$ parts by mass to 100 parts by mass with respect to 100 parts by mass of the polymer before the hydrogenating treatment, and more preferably $1 \times 10^{-2}$ parts by mass to 30 parts by mass.

The solvent which is used for hydrogenation is not particularly limited as long as it dissolves a cyclic olefin polymer and the solvent itself is not hydrogenated and examples thereof include ethers such as tetrahydrofuran, diethyl ether, dibutyl ether, and dimethoxyethane, esters such as ethyl acetate, propyl acetate, or butyl acetate, aromatic hydrocarbons such as benzene, toluene, xylene, and ethyl benzene, aliphatic hydrocarbons such as pentane, hexane, and heptane, aliphatic cyclic hydrocarbons such as cyclopentane, cyclohexane, methyl cyclohexane, dimethyl cyclohexane, and decalin, halogenated hydrocarbons such as methylene dichloride, chloroform, dichloroethane, dichloroethylene, tetrachloroethane, chlorobenzene, and trichlorobenzene, fluorine-containing aromatic hydrocarbons such as fluorobenzene, difluorobenzene, hexafluorobenzene, trifluoromethyl benzene, and metaxylene hexafluoride, fluorine-containing aliphatic hydrocarbons such as perfluorohexane, fluorine-containing aliphatic cyclic hydrocarbons such as perfluorocyclodecalin, or fluorine-containing ethers such as perfluoro-2-butyltetrahydrofuran, and the like. These may be used individually or may be used in a combination of two or more types.

Regarding the hydrogenating reaction of the olefin portion in the main chain described above, the hydrogen pressure is preferably normal pressure to 30 MPa, more preferably 0.5 to 20 MPa, and particularly preferably 2 to 15 MPa. In addition, the reaction temperature is preferably 0° C. to 300° C., more preferably room temperature to 250° C., and particularly preferably 50° C. to 200° C. The manner of carrying out the hydrogenating reaction is not particularly limited; however, examples thereof include a method of hydrogenating by dispersing or dissolving a catalyst in a solvent, a method of hydrogenating by filling a catalyst in a column or the like and circulating a polymerization solution as a stationary phase, and the like.

Furthermore, the hydrogenating treatment of the olefin portion in the main chain is not particularly limited, and a hydrogenating treatment may be performed by precipitating a polymerization solution of the cyclic olefin polymer before in a poor solvent and isolating a polymer and then dissolving it in a solvent again, or a hydrogenating treatment may be performed by the hydrogenating catalyst described above without isolating the polymer from a polymerization solution.

In addition, the hydrogenating ratio of the olefin portion of the cyclic olefin polymer is preferably 50% or more, more preferably 70% to 100%, and particularly preferably 90% to 100%. By setting the hydrogenating ratio to be the lower limit value described above or more, it is possible easily to suppress deterioration which is caused by light absorption or oxygenation caused by heating when molding in the olefin portion and to make the properties of the substrate surface such as a water contact angle favorable.

In a case of using a preferable solid catalyst such as palladium carried on activated carbon and palladium carried on alumina in particular after hydrogenation in the present embodiment, the method for obtaining the cyclic olefin polymer from the polymer solution is not particularly limited, and examples thereof include a method for obtaining a polymer by means such as filtration, centrifugal separation, and decantation and discharging a reaction solution into a poor solvent with stirring, a method of precipitating a polymer by means such as steam stripping which blows steam into a reaction solution, a method of evaporating and removing a solvent from a reaction solution by heating or the like, and the like.

In addition, in a case of carrying out a hydrogenating reaction using a heterogeneous metal carried catalyst, it is possible to obtain a cyclic olefin polymer by the method described above after filtering and separating a metal carried catalyst from the synthesized liquid. Here, a cyclic olefin polymer may be obtained by the method described above after precipitating catalyst components with a large particle diameter in a polymer solution beforehand by means such as decantation or may be obtained after centrifugal separating, taking the supernatant liquid, and filtering the solution from which the catalyst components are mostly taken out. In particular, precise filtering of the catalyst components is favorable and the aperture of the filtering filter is preferably 10 μm to 0.05 μm, particularly preferably 10 μm to 0.1 μm, and even more preferably 5 μm to 0.1 μm.

Next, description will be given of a method for producing medical instrument.

(Method for Producing Medical Instrument Which Uses Fluorine-Containing Cyclic Olefin Polymer)

Description will be given of a method for producing medical instrument for usages in cell culturing or inspection of cells from the fluorine-containing cyclic olefin polymer produced as described above in the present embodiment. For example, it is possible to produce medical instrument of which the water contact angle of the substrate surface of the present embodiment is equal to or more than 70° and equal to or less than 120° by the method which is shown below. The medical instrument according to the present embodiment is provided with, for example, a film, a substrate formed of a single layer film in sheet form, or a substrate obtained by forming a coating film on another material. Examples of the method of producing the substrate include a solution casting method which uses a varnish obtained by dissolving the fluorine-containing cyclic olefin polymer represented by Formula (1) exemplified in the description above in an organic solvent.

Description will be given below of a method for producing a substrate which uses a solution casting method.

Firstly, as described above, a varnish is obtained by dissolving a fluorine-containing cyclic olefin polymer represented by Formula (1) exemplified in the description above in an organic solvent.

The organic solvent is not particularly limited and examples thereof include fluorine-containing aromatic hydrocarbons such as metaxylene hexafluoride, benzotrifluoride, fluorobenzene, difluorobenzene, hexafluorobenzene, trifluoromethylbenzene, and bis(trifluoromethyl)benzene, fluorine-containing aliphatic hydrocarbons such as perfluorohexane and perfluorooctane, fluorine-containing aliphatic cyclic hydrocarbons such as perfluorocyclodecalin, fluorine-containing ethers such as perfluoro-2-butyltetrahydrofuran, halogenated hydrocarbons such as chloroform, chlorobenzene, and trichlorobenzene, ethers such as tetrahydrofuran, dibutyl ether, 1,2-dimethoxyethane, and dioxane, esters such as ethyl acetate, propyl acetate, and butyl acetate, ketones such as methylethyl ketone, methylisobutyl ketone, and cyclohexanone, and the like. It is possible to select from among these in consideration of the solubility and film-forming properties. In addition, the above may be used individually or may be used in a combination of two or more types. In particular, from the point of view of the film-forming property, a solvent which has a boiling point of 70° or more under an atmospheric atmosphere is preferable. Hereby, it is possible to reliably suppress the evaporation rate from being excessively fast. For this reason, it is possible to reliably suppress deterioration of the film thickness precision or unevenness on the film surface, caused by the solvent starting evaporation partially to dry at applying or the like.

The concentration for dissolving the fluorine-containing cyclic olefin polymer is preferably 1.0 to 99.0 mass %, more preferably 5.0 to 90.0 mass %, and particularly preferably 10.0 to 80.0 mass %. The concentration maybe selected in consideration of the solubility of the polymer, the adaptability to the filtration process, the film-forming property, and the thickness of the film.

Furthermore, other components which are known in the art may be added as necessary in a range which does not inhibit the film characteristics in the present embodiment. Examples of the other components include modifiers such as an anti-aging agent, a leveling agent, a wettability modifier, a surfactant, and a plasticizing agent, a stabilizer such as an ultraviolet absorbing agent, a preservative, and an antimicrobial agent, a photo sensitizer, a silane coupling agent, and the like.

Subsequently, the varnish which is prepared by the method described above is filtered by passing through a filter. Hereby, it is possible to greatly reduce polymer insoluble matter, gel, foreign matter, and the like from in the varnish and it is possible to smoothly form the substrate surface as culture apparatus which cultures cells or inspection instrument which performs inspection using the cells and to evenly apply the hydrophobic surface property over the entire surface.

The aperture of the filtering filter is preferably 10 μm to 0.05 μm, particularly preferably 10 μm to 0.1 μm, and even more preferably 5 μm to 0.1 μm. The process of the filtration may be a multi-stage process which sends a polymer solution from a filter with a large hole diameter to a filter with a small hole diameter or may be a single process which directly sends the varnish to a filter with a small hole diameter. The filter material may be formed of an organic material such as Teflon®, PP, PES, or cellulose or may be formed of an inorganic material such as glass fiber or metal and it is possible to select the material from the varnish characteristics and the process adaptability as long as there is no adverse influence on the cell culturing.

In addition, the method of sending varnish to a filter may be a method which uses a pressure difference or may be a method of sending varnish to a filter by mechanical driving via a screw or the like. Furthermore, the filtration temperature is selected from within a range in consideration of the filter performance, the solution viscosity, and the solubility of a polymer and is preferably −10° C. to 200° C., more preferably 0° C. to 150° C., and particularly preferably room temperature to 100° C.

A film is formed from the varnish after filtering the varnish as described above. In a case of production using a solution casting method, the film-forming is carried out by firstly applying a polymer solution (varnish) on a support body by a method such as table coating, spin coating, dip coating, die coating, spray coating, bar coating, roll coating, or curtain flow coating. As the support body, it is possible to select from a support body which is formed of a metal material such as stainless steel and silicon, an inorganic material such as glass and quartz, a resin material such as polyimide, polyamide, polyester, polycarbonate, polyphenylene ether, polyphenylene sulfide, polyacrylate, polymethacrylate, polyacrylate, epoxy resin, and silicone resin, and the like.

Regarding drying the coated film, drying by heating may be carried out by placing a support body casted a solution on a heated plate, drying by heating may be carried out by placing a casted substrate of a solution in a heated drying oven, drying may be carried out by blowing warm gas such as air and nitrogen which is heated onto a coated film, or drying may be carried out using a process combining the above. The temperature when drying is preferably 10° C. to 250° C., more preferably 20° C. to 220° C., and particularly preferably 30° C. to 200° C. and is selected in consideration of the characteristics of the varnish, the film thickness of the film, and the heat resistance of the substrate. In addition, a coated film may be dried by setting multi-stage drying temperatures with two or more types of temperature settings. It is possible to select the time of drying the coated film from conditions in consideration of the boiling point of the varnish solvent, the thickness of the film, and the processing conditions. Hereby, a film is formed on a support body.

In a case of obtaining a film or a sheet substrate in a single layer, for example, it is possible to produce a film or sheet substrate by separating from a support body. The separation from a support body may be performed by adhering a commercially available tape on an end section of it, applying pressure thereto and then separating or may be separated it by using the difference in surface tension between the support body surface and the contact surface of it how bringing a liquid such as water or a solvent into the contact interface between the film and the support body and contacting them each.

In a case of obtaining a substrate by forming a coated film on another material as the support body, it is possible to produce a substrate which is formed of a coated film on the support body and the fluorine-containing cyclic olefin polymer of the present embodiment, for example, by carrying out the described steps above up to the step of drying the coated film. In this case, the support body is particularly preferably selected from an organic material such as PET or an acrylic resin or an inorganic material such as glass and silicon.

In addition, examples of the method of producing a substrate which configures other medical instrument include a method of producing a film as a substrate by a melt molding method. Examples of the method of producing a film by a melt molding method include a method of making a film of the fluorine-containing cyclic olefin polymer which is exemplified in the description above via a T die using a melt kneading apparatus, an inflation method, or the like.

In melt-extruded film production using a T die, for example, it is possible to carry out processing into a film by placing a cyclic olefin polymer in which an additive agent is blended as necessary in an extruding apparatus, melting and kneading at a temperature which is preferably 50° C. to 200° C. higher than the glass transition temperature, and more preferably 80° C. to 150° C. higher, extruding from the T die, and cooling the melted polymer with a cooling roll or the like. In addition, an additive agent such as an ultraviolet absorbing agent, an antioxidant, a flame retardant, an anti-static agent, and a coloring agent may be added within a range which does not inhibit the effects of the present invention.

The film thickness which is produced using the fluorine-containing cyclic olefin polymer is preferably 1 to 1000 μm, more preferably 5 to 500 μm, and particularly preferably 10 to 200 μm. These are favorable ranges from the point of view of producing medical instrument which is used for cell culturing such as, for example, a culture bag, a culture plate, and a culture petri dish. In addition, it is possible to set the film thickness to fit a process of producing the equipment.

From a film produced by a solution casting method or a melt molding method, it is possible to manufacture the medical instrument, for example, in the form of a bag, tube, or the like by using a heat sealing method, a sealing method which uses an adhesive agent, or the like and, additionally, it is also possible to manufacture the medical instrument, for example, in a form of a petri dish or the like by a method such as melt pressing.

Furthermore, by using the fluorine-containing cyclic olefin polymer which is exemplified in the description above, it is also possible to manufacture culture apparatus such as a petri dish, a multi-well plate, and a flask for cell culturing, for example, by a method such as injection molding, press molding, compression molding, injection compression molding, extrusion molding, or blow molding. The melt molding temperature at this time is preferably 330° C. or lower, more preferably 300° C. or lower, and particularly preferably 280° C. or lower. It is possible to more reliably suppress yellowing accompanying thermal decomposition of the polymer, generation of decomposition gas, and the like by melting and molding a polymer at a temperature in these ranges. Furthermore, additive agents such as an ultraviolet absorbing agent, an antioxidant, a flame retardant, an anti-static agent, and a coloring agent may be added within a range which does not inhibit the effects of the present invention.

In addition, the medical instrument which uses the fluorine-containing cyclic olefin polymer according to the present embodiment may be provided with, for example, a film or a substrate formed of a single layer film or sheet form in which a convex-concave structure is formed on the surface on which cells are held or in contact, or a substrate formed and obtained by adhering a film or a single layer film or sheet form in which a convex-concave structure is formed on another material using an adhesive agent or a pressure sensitive adhesive, or the like, and is particularly preferably used to realize the instrument with a water contact angle of 121° to 160°.

Regarding the size of the convex-concave structure, a pattern of which the distance between convexities is 40 nm to 90 μm, preferably 60 nm to 80 μm, particularly preferably 80 nm to 70 μm, is shaped and then it is possible to make the water contact angle be in the desired range and the shape is not particularly limited.

Here, the convex-concave structure may be formed by various types of methods such as screen printing, an embossing process, submicron imprinting, and nano imprinting or the like.

In particular, when forming the convex-concave structure using an imprint method, examples thereof include a solution casting method which applies varnish, which is obtained by dissolving the fluorine-containing cyclic olefin polymer which contains a structure unit represented by Formula (1) exemplified in the description above in an organic solvent, on various patterns of molds which are formed of quartz, silicon, nickel, resists, or the like.

Description will be given below of a method for producing a substrate formed a convex-concave structure from the varnish by a solution casting method.

Firstly, the varnish is prepared by dissolving the fluorine-containing cyclic olefin polymer which contains the structure unit represented by Formula (1) in an organic solvent using the same method as the method for producing a substrate which uses the solution casting method described above and then filtrating by passing the result through a filter.

Next, it is possible to obtain a substrate formed a convex-concave structure which is transcribed the pattern of the mold by bringing the varnish into contact with the pattern surface of a mold in which a convex-concave structure is formed and then evaporating a solvent.

Examples of the substrate material of the mold having a fine pattern on the surface, which is used for producing the substrate in which the convex-concave structure of the present embodiment, include metal materials such as nickel, iron, stainless steel, germanium, titanium, and silicon, inorganic materials such as glass, quartz, and alumina, resin materials such as polyimide, polyamide, polyester, polycarbonate, polyphenylene ether, polyphenylene sulfide, polyacrylate, polymethacrylate, polyarylate, an epoxy resin, and a silicone resin, carbon materials such as diamond and graphite, and the like.

The method how to contact the varnish in which the fluorine-containing cyclic olefin polymer having the structure unit represented by Formula (1) of the present embodiment is dissolved in an organic solvent with the mold is not particularly limited and may be either a method of applying the polymer solution (varnish) on a fine pattern surface of a mold by means such as table coating, spin coating, die coating, spray coating, bar coating, and roll coating or a method of applying a polymer solution on a substrate of metal materials such as stainless steel and silicon, inorganic materials such as glass and quartz, resin materials such as polyimide, polyamide, polyester, polycarbonate, polyphenylene ether, polyphenylene sulfide, polyacrylate, polymethacrylate, polyarylate, an epoxy resin, and a silicone resin, or the like by means such as table coating, spin coating, die coating, spray coating, bar coating, and roll coating and then covering the fine pattern surface of the mold so as to be brought into contact therewith.

In detail, examples thereof include a method (1) which includes a step of applying a solution (varnish) made of a fluorine-containing cyclic olefin polymer and an organic solvent on a mold surface having a fine pattern and a step of evaporating the solvent from the solution, and a method (2) which includes a step of applying a solution (varnish) made of a fluorine-containing cyclic olefin polymer and an organic solvent on a support body (a substrate), a step of pressing the upper surface of the applied layer with the mold surface having the formed fine pattern, and a step of evaporating the solvent from the applied layer, and the like. Here, in the method (2), it is also possible to pressurize by the mold after evaporating the solvent from the applied layer.

It is possible to carry out the method with the temperature for evaporating the solvent from a transcribed body and drying in the range of generally 10° C. to 300° C., preferably 50° C. to 200° C., the pressure generally in the range of 133 Pa to atmospheric atmosphere, and moreover with a drying time which is generally 10 minutes to 120 hours, preferably in the range of 30 minutes to 48 hours. In addition, the drying temperature, pressure, and time may be changed in step by step with individual settings.

In the present embodiment, a step of separating the transcribed body after forming the transcribed body on a mold by evaporating the solvent is provided. The separation of the transcribed body is preferably performed at a temperature of a glass transition temperature or lower and moreover, the separation is more preferably, no higher than (glass transition temperature −20° C.) and it is possible to hold a pattern shape which is formed on the transcribed body with high precision and easily separated by this means. Regarding the separation method, it is possible to separate by releasing it from the mold through hand separation or by using the difference of surface tension after contacting the transcribed body on the mold by means, for example, such as dipping in or spraying with a medium such as water and the like. In addition, a resin material or an inorganic material such as glass may be attached to the back side of transcribed body, and it may be released as a support material.

In addition, in the present embodiment, it is also possible to obtain the substrate formed the convex-concave structure on the surface, on which the cells are held or in contact, by transcribing the pattern of the mold on a film made of a fluorine-containing cyclic olefin polymer having the structure unit represented by Formula (1) due to contacting with the pattern surface of the mold and pressing thereon.

For example, a method of pressing with the mold which is heated at higher than a glass transition temperature of a film, a method of heating a film at higher than a glass transition temperature of it and then pressing with a mold, or a method of heating a film and a mold at higher than a glass transition temperature and pressing with the mold is preferable, the heating temperature is in the range of the glass transition temperature to (the glass transition temperature+100° C.), preferably (the glass transition temperature+5° C.) to (the glass transition temperature+50° C.), moreover, the pressing pressure is generally 1 MPa to 100 MPa, preferably in the range of 1 MPa to 60 MPa. Hereby, it is possible to form the pattern shape on the transcribed body with a high precision.

The separation of the transcribed body made by pressing with the mold is preferably performed at the temperature lower than the glass transition temperature and is more preferably carried out at the temperature lower than (the glass transition temperature −20° C.). Hereby, it is possible for the transcribed body with a high precise pattern shape to easily carry out the separation. Regarding the separation method, it is possible to separate by releasing it from the mold through hand separation or by using the difference of surface tension after contacting the transcribed body on the mold by means, for example, such as dipping in or spraying with a medium such as water and the like. In addition, a resin material or an inorganic material such as glass maybe attached to the back side of transcribed body, and it may be released as a support material.

Furthermore, examples thereof include a method of producing a film which is a substrate having a convex-concave structure by a melt molding method. Examples of a method for producing a film by a melt molding method include a method of making the fluorine-containing cyclic olefin polymer exemplified in the description above into a film via a T die using a melt kneading apparatus. In melt-extruded film production using a T die, for example, it is possible to carry out processing into a film having a convex-concave structure is formed by placing a cyclic olefin polymer in which an additive agent is blended as necessary in an extruding apparatus, melting and kneading at a temperature which is preferably 50° C. to 200° C. higher than the glass transition temperature, more preferably 80° C. to 150° C. higher than the glass transition temperature, extruding from the T die, and pressing it with a mold in a roll shape having a fine pattern on the surface, which is heated at higher than a glass transition temperature of the polymer, onto the film as feeding by a cold roll. The heating temperature of the roll having a fine pattern on the surface at this time is applied in the same range as the heating temperature at the time of forming the convex-concave structure by heating and pressing the film with the mold described above. In addition, an additive agent such as an ultraviolet absorbing agent, an antioxidant, a flame retardant, an anti-static agent, and a coloring agent may be added within a range which does not inhibit the effects of the present invention.

The film thickness of the substrate with a surface having the convex-concave structure on which the cells are held or in contact, which is produced using a fluorine-containing cyclic olefin polymer is formed is preferably 1 to 1000 μm, more preferably 5 to 500 μm, and particularly preferably 10 to 200 μm. These are favorable ranges from the point of view of producing medical instrument which is used for, for example, cell culturing such as a culture bag, a culture plate, and a culture petri dish. In addition, it is possible to set the film thickness to fit a process of producing the equipment.

The film thickness which is produced using the fluorine-containing cyclic olefin polymer is preferably 1 to 1000 μm, more preferably 5 to 500 μm, and particularly preferably 10 to 200 μm. These are favorable ranges from the point of view of producing medical instrument which is used for cell culturing such as, for example, a culture bag, a culture plate, and a culture petri dish.

In addition, it is possible to set the film thickness to fit a process of producing the equipment.

From a film or a sheet produced by a solution casting method, a heating and pressing method, or a melt molding method on which the convex-concave structure is formed, it is possible to manufacture medical instrument, for example, in a form of a bag, tube, or the like by a heat sealing method, a sealing method which uses an adhesive agent, and the like. In addition, it is also possible to produce medical instrument like a form of a film or sheet on which the convex-concave structure of the present embodiment is adhered to a surface, on which cells are held or in contact, of the substrate of the medical instrument such as, for example, a petri dish, a multi-well plate, or a flask made of other material such as polystyrene, polyethylene and metals.

(Method for Producing Medical Instrument Which Uses Fluorine-containing Cyclic Olefin Polymer Composition)

Next, description will be given of a method for producing medical instrument which is used for cell culturing or inspection of cells from a fluorine-containing cyclic olefin polymer composition in the present embodiment. For example, it is possible to produce medical instrument of which the water contact angle of the substrate surface of the present embodiment is equal to or more than 70° and equal to or less than 120° by the method which is shown below.

The fluorine-containing cyclic olefin polymer composition includes a fluorine-containing cyclic olefin polymer (also referred to below as a fluorine-containing cyclic olefin polymer (A)) represented by Formula (1) exemplified in the description above, a photocurable compound (B), and a photo-curing initiator (C). According to the present embodiment, it is possible to form at least a surface of the substrate of the medical instrument on which cells are in contact or held on a surface of the substrate using the fluorine-containing cyclic olefin polymer composition.

Hereby, it is possible to modify the properties of the substrate surface, on which cells are in contact or held, in various types of culture apparatus such as a cell culture bag or a plate as exhibiting the strong adhesion with various types of materials and to provide medical instrument which is able to allow cell proliferation as suppressing the adhesion and attachment of the cells.

The medical instrument according to the present embodiment is provided with, for example, a substrate which is formed by a film or a single layer film in sheet form or a substrate which is obtained by forming a coated film on other material. Examples of the method of producing the substrate include a solution casting method which uses varnish which is obtained by dissolving a fluorine-containing cyclic olefin polymer composition included the fluorine-containing cyclic olefin polymer (A) in an organic solvent.

Description will be given below of a method for producing a substrate which uses a solution casting method.

Firstly, as described above, varnish is obtained by dissolving a fluorine-containing cyclic olefin polymer composition included the fluorine-containing cyclic olefin polymer (A) in an organic solvent.

A varnish of the fluorine-containing cyclic olefin polymer composition according to the present embodiment is obtained, for example, by preparing the fluorine-containing cyclic olefin polymer (A) in a solution at an arbitrary concentration beforehand, adding and mixing the photocurable compound (B) such as the mass ratio (A)/(B) of the fluorine-containing cyclic olefin polymer (A) to the photocurable compound (B) described below is preferably 99.9/0.1 to 50/50, more preferably 99. 9/0. 1 to 55/45, and particularly preferably 99.9/0.1 to 60/40.

The organic solvent which is used when preparing the fluorine-containing cyclic olefin polymer composition is not particularly limited and examples thereof include fluorine-containing aromatic hydrocarbons such as metaxylene hexafluoride, benzotrifluoride, fluorobenzene, difluorobenzene, hexafluorobenzene, trifluoromethylbenzene, bis(trifluoromethyl)benzene, and metaxylene hexafluoride, fluorine-containing aliphatic hydrocarbons such as perfluorohexane and perfluorooctane, fluorine-containing aliphatic cyclic hydrocarbons such as perfluorocyclodecalin, fluorine-containing ethers such as perfluoro-2-butyl tetrahydrofuran, halogenated hydrocarbons such as chloroform, chlorobenzene, and trichlorobenzene, ethers such as tetrahydrofuran, dibutyl ether, 1,2-dimethoxyethane, dioxane, propylene glycol monomethyl ether, dipropylene glycol monomethyl ether, and propylene glycol monomethyl ether acetate, esters such as ethyl acetate, propyl acetate, and butyl acetate, ketones such as methylethyl ketone, methylisobutyl ketone, and cyclohexanone, alcohols such as methanol, ethanol, isopropyl alcohol, 2-methoxy ethanol, and 3-methoxy propanol, and the like. It is possible to select from among these in consideration of the solubility and film-forming properties. In addition, the above may be used individually or may be used in a combination of two or more types. In particular, from the point of view of the film-forming property, a solvent which has a boiling point of 70° or more under atmospheric pressure is preferable. Hereby, it is possible to reliably suppress the evaporation rate from being excessively fast. For this reason, it is possible to reliably suppress deterioration of the film thickness precision or unevenness on the film surface, caused by the solvent starting to partially dry during application.

Here, it is also possible to add components known in the art other than the fluorine-containing cyclic olefin polymer (A), the photocurable compound (B), and the photo-curing initiator (C) to the fluorine-containing cyclic olefin polymer composition as necessary. Examples of the components include modifiers such as anti-aging agents, leveling agents, wettability modifiers, surfactants, and plasticizing agents, stabilizers such as an ultraviolet absorbing agents, preservatives, antimicrobial agents, photo sensitizers, silane coupling agents, and the like.

(Photocurable Compound (B))

In the fluorine-containing cyclic olefin polymer composition, the mass ratio (A)/(B) of the fluorine-containing cyclic olefin polymer (A) and the photocurable compound (B) is preferably 99.9/0.1 to 50/50, more preferably 99.9/0.1 to 55/45, and even more preferably 99.9/0.1 to 60/40. Examples of the photocurable compound (B) include a compound which has a reactive double bond group, a cationically polymerizable ring opening polymerizable compound, and the like. A cationically polymerizable ring opening polymerizable compound is preferably selected from the point of view of suppression of substrate deformation which comes along with volume contraction after being cured when applied to be used or of the compatibility with the fluorine-containing cyclic olefin polymer (A).

A compound which has a reactive double bond group and a cationically polymerizable ring opening polymerizable compound may have one reactive group in one molecule or may have a plurality thereof. In addition, compounds with different numbers of reactive groups may be blended in the photocurable compound (B) at an arbitrary ratio and used. Furthermore, compounds which have a reactive double bond group and a cationically polymerizable ring opening polymerizable compound may be blended and used as the photocurable compound (B) at an arbitrary ratio. Hereby, it is possible to adhere firmly and the fluorine-containing cyclic olefin polymer composition of the present embodiment with dimensional accuracy to a component which is formed by another material. In addition, it is possible to favorably obtain medical instrument as a substrate for cell culturing or inspecting cells which is able to realize the effects of the present embodiment.

Examples of the cationically polymerizable ring-opening polymerizable compounds in the photocurable compounds (B) include epoxy compounds such as alicyclic epoxy resins such as cyclohexene epoxide, dicyclopentadiene oxide, limonene dioxide, 4-vinylcyclohexene dioxide, 3,4-epoxycyclohexylmethyl-3',4'-epoxycyclohexane carboxylate, di(3,4-epoxycyclohexyl)adipate, (3,4-epoxycyclohexyl)methyl alcohol, (3,4-epoxy-6-methylcyclohexyl)methyl-3,4-epoxy-6-methylcyclohexane carboxylate, ethylene-1,2-di(3,4-epoxycyclohexane carboxylic acid) ester, (3,4-epoxycyclohexyl)ethyl trimethoxy silane, phenyl glycidyl ether, dicyclohexyl-3,3'-diepoxide, 1,7-octadiene diepoxide, bisphenol A type epoxy resin, halogenated bisphenol A type epoxy resin, bisphenol F type epoxy resin, o-, m-, p-cresol novolac type epoxy resins, phenol novolac type epoxy resin, polyglycidyl ethers of polyhydric alcohols, and 3,4-epoxy-cyclohexenyl methyl-3',4'-epoxy cyclohexene carboxylate, or epoxy compounds such as glycidyl ether of hydrogenated bisphenol A; 3-methyl-3-(butoxymethyl)oxetane,
3-methyl-3-(pentyloxymethyl)oxetane,
3-methyl-3-(hexyloxymethyl)oxetane,
3-methyl-3-(2-ethylhexyloxymethyl)oxetane,
3-methyl-3-(octyloxycarboxymethyl)oxetane,
3-methyl-3-(decanyloxymethyl)oxetane,
3-methyl-3-(dodecanyloxymethyl)oxetane,
3-methyl-3-(phenoxymethyl)oxetane,
3-ethyl-3-(butoxymethyl)oxetane,
3-ethyl-3-(pentyloxymethyl)oxetane,
3-ethyl-3-(hexyloxymethyl)oxetane,
3-ethyl-3-(2-ethylhexyloxymethyl)oxetane,
3-ethyl-3-(octyloxymethyl)oxetane,
3-ethyl-3-(decanyloxymethyl)oxetane,
3-ethyl-3-(dodecanyloxymethyl)oxetane,
3-(cyclohexyloxymethyl)oxetane,
3-methyl-3-(cyclohexyloxymethyl)oxetane,
3-ethyl-3-(cyclohexyloxymethyl)oxetane,
3-ethyl-3-(phenoxymethyl)oxetane, 3,3-dimethyl oxetane, 3-hydroxymethyl oxetane, 3-methyl-3-hydroxymethyl oxetane, 3-ethyl-3-hydroxymethyl oxetane, 3-ethyl-3-phenoxymethyl oxetane, 3-n-propyl-3-hydroxymethyl oxetane, 3-isopropyl-3-hydroxymethyl oxetane, 3-n-butyl-3-hydroxymethyl oxetane,
3-isobutyl-3-hydroxymethyl oxetane, 3-sec-butyl-3-hydroxymethyl oxetane, 3-tert-butyl-3-hydroxymethyl oxetane,
3-ethyl-3-(2-ethylhexyl)oxetane, or the like, and as a compound which has two or more oxetanyl groups, examples include oxetane compounds such as bis(3-ethyl-3-oxetanylmethyl)ether,
1,2-bis[(3-ethyl-3-oxetanylmethoxy)]ethane,
1,3-bis[(3-ethyl-3-oxetanylmethoxy)]propane,
1,3-bis[(3-ethyl-3-oxetanylmethoxy)]-2,2-dimethyl-propane,
1,4-bis(3-ethyl-3-oxetanylmethoxy)butane,
1,6-bis(3-ethyl-3-oxetanylmethoxy)hexane,
1,4-bis[(3-methyl-3-oxetanyl)methoxy]benzene,
1,3-bis[(3-methyl-3-oxetanyl)methoxy]benzene,
1,4-bis{[(3-methyl-3-oxetanyl)methoxy]methyl}benzene,
1,4-bis{[(3-methyl-3-oxetanyl)methoxy]methyl}cyclohexane,
4,4'-bis{[(3-methyl-3-oxetanyl)methoxy]methyl}biphenyl,
4,4'-bis{[(3-methyl-3-oxetanyl)methoxy]methyl}bicyclohexane,
2,3-bis[(3-methyl-3-oxetanyl)methoxy]bicyclo[2.2.1]heptane,
2,5-bis[(3-methyl-3-oxetanyl)methoxy]bicyclo[2.2.1]heptane,
2,6-bis[(3-methyl-3-oxetanyl)methoxy]bicyclo[2.2.1]heptane,
1,4-bis[(3-ethyl-3-oxetanyl)methoxy]benzene,
1,3-bis[(3-ethyl-3-oxetanyl)methoxy]benzene,
1,4-bis{[(3-ethyl-3-oxetanyl)methoxy]methyl}benzene,
1,4-bis{[(3-ethyl-3-oxetanyl)methoxy]methyl}cyclohexane,
4,4'-bis{[(3-ethyl-3-oxetanyl)methoxy]methyl}biphenyl,
4,4'-bis{[(3-ethyl-3-oxetanyl)methoxy]methyl}bicyclohexane,
2,3-bis[(3-ethyl-3-oxetanyl)methoxy]bicyclo[2.2.1]heptane,
2,5-bis[(3-ethyl-3-oxetanyl)methoxy]bicyclo[2.2.1]heptane, and
2,6-bis[(3-ethyl-3-oxetanyl)methoxy]bicyclo[2.2.1]heptane.
The above may be used individually or may be used in a combination of two or more types.

In addition, examples of the compound which has a reactive double bond group in the photocurable compound (B) include olefins such as fluorodiene ($CF_2=CFOCF_2CF_2CF=CF_2$, $CF_2=CFOCF_2CF(CF_3)CF=CF_2$, $CF_2=CFCF_2C(OH)(CF_3)CH_2CH=CH_2$, $CF_2=CFCF_2C(OH)(CF_3)CH=CH_2$, $CF_2=CFCF_2C(CF_3)(OCH_2OCH_3)CH_2CH=CH_2$, $CF_2=CFCH_2C(C(CF_3)_2OH)(CF_3)CH_2CH=CH_2$); cyclic olefins such as norbornene and norbornadiene; alkyl vinyl ethers such as cyclohexylmethyl vinyl ether, isobutyl vinyl ether, cyclohexyl vinyl ether, and ethyl vinyl ether; vinyl esters such as vinyl acetate; (meth) acrylic acid such as (meth) acrylic acid, phenoxyethyl acrylate, benzyl acrylate, stearyl acrylate, lauryl acrylate, 2-ethylhexyl acrylate, allyl acrylate, 1,3-butanediol diacrylate, 1,4-butanediol diacrylate, 1,6-hexane diol diacrylate, trimethylol propane triacrylate, pentaerythritol triacrylate, dipentaerythritol hexaacrylate, ethoxy ethyl acrylate, methoxyethyl acrylate, glycidyl acrylate, tetrahydrofurfuryl acrylate, diethylene glycol diacrylate, neopentyl glycol diacrylate, polyoxyethylene glycol diacrylate, tripropylene glycol diacrylate, 2-hydroxyethyl acrylate, 2-hydroxypropyl acrylate, 4-hydroxybutyl vinyl ether, N,N-diethylaminoethyl acrylate, N,N-dimethylaminoethyl acrylate, N-vinylpyrrolidone, and dimethyl aminoethyl methacrylate, and derivatives thereof, or fluorine-containing acrylates thereof, or the like. The above may be used individually or may be used in a combination of two or more types.

(Photo-Curing Initiator (C))

Examples of the photo-curing initiator (photopolymerization initiator) (C) include cationic photoinitiators which generate cations when irradiated with light, photoradical initiators which generate radicals when irradiated with light, and the like. The usage amount of the photo-curing initiator (C) is preferably 0.05 parts by mass or more with respect to 100 parts by mass of the photocurable compound (B), and more preferably from 0.1 to 10 parts by mass.

The cationic photoinitiator which generates cations when irradiated with light of the photo-curing initiator (C) is not particularly limited as long as it is a compound which initiates cationic polymerization of cationically polymerizable ring-opening compounds polymerizable when irradiated with light; however, for example, compounds which undergo a photoreaction and release Lewis acid such as onium salts with anions which form a pair with onium cations are preferable.

Specific examples of the onium cations include diphenyliodonium, 4-methoxy-diphenyliodonium, bis(4-methylphenyl)iodonium, bis(4-tert-butylphenyl)iodonium, bis(dodecylphenyl)iodonium, triphenylsulfonium, diphenyl-4-thiophenoxyphenyl sulfonium, bis[4-(diphenyl sulfonio)-phenyl]sulfide, bis[4-(di(4-(2-hydroxyethyl)phenyl) sulfonio)-phenyl]sulfide, $\eta^5$-2,4-(cyclopentadienyl)[1,2,3,4,5,6-$\eta$-(methylethyl)benzene]-iron (1+), and the like. In addition, other than the onium cations, examples include perchlorate ions, trifluoromethanesulfonate ions, toluene sulfonate ions, trinitrotoluene sulfonate ions, and the like. In addition, these cationic photoinitiators may be used alone or may be used in a combination of two or more.

On the other hand, specific examples of anions include tetrafluoroborate, hexafluorophosphate, hexafluoroantimonate, hexafluoroarsenate, hexachloroantimonate, tetra(fluorophenyl)borate, tetra(difluorophenyl)borate, tetra(trifluorophenyl)borate, tetra(tetrafluorophenyl)borate, tetra(pentafluorophenyl)borate, tetra(perfluorophenyl)borate, tetra(trifluoromethylphenyl)borate, tetra[di(trifluoromethyl)phenyl]borate, and the like. In addition, these cationic photoinitiators may be used alone or may be used in a combination of two or more.

Further specific examples of preferably used cationic photoinitiators include IRGACURE 250 (produced by BASF), IRGACURE 784 (produced by BASF), ESACURE 1064 (produced by Orchid Bell Tea Co., Ltd.), WPI-124 (produced by Wako Pure Chemical Industries Ltd.), CYRAURE UVI6990 (produced by Union Carbide Japan Corporation), CPI-100P (San-Apro Ltd.), ADEKAOPTOMER SP-172 (Adeka Corporation), ADEKAOPTOMER SP-170 (Adeka Corporation), ADEKAOPTOMER SP-152 (Adeka Corporation), ADEKAOPTOMER SP-150 (Adeka Corporation), and the like. In addition, these cationic photoinitiators maybe used alone or may be used in a combination of two or more.

In addition, examples of photo-radical initiators generating radicals when irradiated with light in the photo-curing initiator (C) include acetophenones such as acetophenone, p-tert-butyl trichloroacetophenone, chloroacetophenone, 2,2-diethoxyacetophenone, hydroxyacetophenone, 2,2-dimethoxy-2'-phenyl acetophenone, 2-aminoacetophenone, and dialkylamino acetophenone; benzoins such as benzoin, benzoin methyl ether, benzoin ethyl ether, benzoin isopropyl ether, benzoin isobutyl ether, 1-hydroxy cyclohexyl phenyl ketone, 2-hydroxy-2-methyl-1-phenyl-2-methylpropan-1-one, 1-(4-isopropylphenyl)-2-hydroxy-2-methylpropan-1-one; benzophenones such as benzophenone, benzoyl benzoic acid, methyl benzoyl benzoic acid, methyl-o-benzoyl benzoate, 4-phenyl benzophenone, hydroxybenzophenone, hydroxypropyl benzophenone, acrylic benzophenone, and 4,4'-bis(dimethylamino) benzophenone; thioxanthones such as thioxanthone, 2-chlorothioxanthone, 2-methylthioxanthone, diethylthioxanthone, and dimethyl thioxanthone; fluorine-based peroxides such as perfluoro (tert-butyl peroxide), perfluoro benzoyl peroxide; a-acyl oxime ester, benzyl-(o-ethoxycarbonyl)-a-monoxime, acyl phosphine oxide, glyoxy ester, 3-ketocoumarin, 2-ethyl anthraquinone, camphor quinone, tetramethyl thiuram sulfide, azobisisobutyronitrile, benzoyl peroxide, dialkyl peroxide, tert-butyl peroxypivalate, and the like.

Specific examples of more preferably used photoradical initiators include IRGACURE 651 (produced by BASF), IRGACURE 184 (produced by BASF), DAROCUR 1173 (produced by BASF), benzophenone, 4-phenyl benzophenone, IRGACURE 500 (produced by BASF), IRGACURE 2959 (produced by BASF), IRGACURE 127 (produced by BASF), IRGACURE 907 (produced by BASF), IRGACURE 369 (produced by BASF), IRGACURE 1300 (produced by BASF), IRGACURE 819 (produced by BASF), IRGACURE 1800 (produced by BASF), DAROCUR TPO (produced by BASF), DAROCUR 4265 (produced by BASF), IRGACURE OXE01 (produced by BASF), IRGACURE OXE02 (produced by BASF), ESACURE KT55 (produced by Orchid Bell Tea Co., Ltd.), ESACURE KIP150 (produced by Orchid Bell Tea Co., Ltd.), ESACURE KIP100F (produced by Orchid Bell Tea Co., Ltd.), ESACURE KT37 (produced by Orchid Bell Tea Co., Ltd.), ESACURE KTO46 (produced by Orchid Bell Tea Co., Ltd.), ESACURE 1001M (produced by Orchid Bell Tea Co., Ltd.), ESACURE KIP/EM (produced by Orchid Bell Tea Co., Ltd.), ESACURE DP250 (produced by Orchid Bell Tea Co., Ltd.), ESACURE KB1 (produced by Orchid Bell Tea Co., Ltd.), 2,4-diethyl thioxanthone, and the like. Among the above, examples of more preferably used photoradical polymerization initiators include IRGACURE 184 (produced by BASF), DAROCUR 1173 (produced by BASF), IRGACURE 500 (produced by BASF), IRGACURE 819 (produced by BASF), DAROCUR TPO (produced by BASF), ESACURE KIP100F (produced by Orchid Bell Tea Co., Ltd.), ESACURE KT37 (produced by Orchid Bell Tea Co., Ltd.) and ESACURE KT046 (produced by Orchid Bell Tea Co., Ltd.). In addition, these photo-radical initiators may be used alone or may be used in a combination of two or more.

The photocurable compound (B) and photo-curing initiator (C) can be used as a photocurable composition which contains the above photocurable compound (B) and photo-curing initiator (C). The photocurable composition can be obtained by dissolving the photo-curing initiator (C) in the photocurable compound (B) and can also be obtained by dissolving the photocurable compound (B) and photo-curing initiator (C) in an organic solvent together. Furthermore, other known components maybe added as a third component as necessary, for example, modifiers such as anti-aging agents, leveling agents, wettability improving agents, surfactants, plasticizers, stabilizers such as ultraviolet absorbers, preservatives, antimicrobial agents, photosensitizers, silane coupling agents, and the like.

The organic solvent used to prepare the photocurable composition is not particularly limited and examples thereof include fluorine-containing aromatic hydrocarbons such as metaxylene hexafluoride, benzotrifluoride, fluorobenzene, difluorobenzene, hexafluorobenzene, trifluoromethyl benzene, bis(trifluoromethyl)benzene, and metaxylene hexafluoride, fluorine-containing aliphatic hydrocarbons such as perfluorohexane and perfluorooctane, fluorine-containing aliphatic cyclic hydrocarbons such as perfluorocyclohexyl decalin, fluorine-containing ethers such as perfluoro-2-butyl tetrahydrofuran, halogenated hydrocarbons such as chloroform, chlorobenzene, and trichlorobenzene, ethers such as tetrahydrofuran, dibutyl ether, 1,2-dimethoxyethane, dioxane, propylene glycol monomethyl ether, dipropylene glycol monomethyl ether, and propylene glycol monomethyl ether acetate, esters such as ethyl acetate, propyl acetate, and butyl acetate, or ketones such as methylethyl ketone, methyl isobutyl ketone, and cyclohexanone, alcohols such as methanol, ethanol, isopropyl alcohol, 2-methoxy ethanol, and 3-methoxy propanol, and the like. Selection from among these is possible in consideration of the solubility and the film-forming properties, and an organic solvent dissolving the fluorine-containing cyclic olefin polymer (A) in it may be the same or different, and may be used in a combination of two or more. In particular, the solvent preferably has a boiling point of 70° C. or higher at atmospheric pressure from the point of view of the film-forming properties. Hereby, it is possible to reliably suppress the evaporation rate from being excessively fast. For this reason, it is possible to reliably suppress deterioration of the film thickness precision or unevenness on the film surface, caused by the solvent starting to partially dry when applying, or the like.

Since the fluorine-containing cyclic olefin polymer composition in the present embodiment uses a specific fluorine-containing cyclic olefin polymer which has a hydrocarbon structure in the main chain and a fluorine-containing aliphatic cyclic structure in the side chain, it has the big polarity and is also possible to produce a substrate having the good compatibility with a photocurable compound and a photo-curing initiator maintaining good transparent in the form after being cured. In addition, by being material which has a fluorine-containing cyclic olefin polymer as a substrate, it is possible to maintain the water contact angle of the substrate surface at 70° to 160°. Hereby, it is possible for cells in the culturing of various types of cells or the inspection of various types of cells to proliferate with suppressing adherence or attachment of the cells to a substrate made of a fluorine-containing cyclic olefin polymer composition.

In addition, regarding the fluorine-containing cyclic olefin polymer composition, it is possible to modify the surface hardness to be harder by the photocurable compound forming a three-dimensional mesh structure in a form after being cured. For this reason, it is possible to improve the scratch property in a case of implementation in medical instrument or the like and convenient use is possible when used as a substrate for cell culturing or inspection of cells.

Subsequently, the varnish which is prepared by the method described above is filtered by passing through a filter. Hereby, it is possible to reduce greatly polymer insoluble matter, gel, foreign matter, and the like from the varnish and it is possible to form smoothly the substrate surface of culture apparatus for cell culturing and make the hydrophobic surface property even over the entire surface.

The aperture of the filtering filter is preferably 10 μm to 0.05 μm, particularly preferably 10 μm to 0.1 μm, and even more preferably 5 μm to 0.1 μm. The process of the filtration may be a multi-stage process which sends a polymer solution from a filter with a large hole diameter to a filter with a small hole diameter or may be a single process which directly sends the varnish to a filter with a small hole diameter. The material of the filter may be formed of an organic material such as Teflon®, PP, PES, or cellulose or may be formed of an inorganic material such as glass fiber or metal and it is possible to select the material from the varnish characteristics and the process adaptability as long as there is no influence on the cell culturing.

In addition, the method of sending varnish to a filter may be a method which uses a pressure difference or may be a method of sending varnish to a filter by mechanical driving via a screw or the like. Furthermore, the filtration temperature is selected in a range in consideration of the filter performance, the solution viscosity, the heat stability of a photocurable compound, and the solubility of a polymer and is preferably −10° C. to 200° C., more preferably 0° C. to 150° C., and particularly preferably room temperature to 100° C.

A film is formed from the varnish after filtering the varnish as described above. In a case of production by a solution casting method, film is formed by firstly applying a polymer solution (varnish) on a support body by a method such as table coating, spin coating, dip coating, die coating, spray coating, bar coating, roll coating, or curtain flow coating. Examples of the support body include support bodies formed of a metal material such as stainless steel and silicon, an inorganic material such as glass and quartz, a resin material such as polyimide, polyamide, polyester, polycarbonate, polyphenylene ether, polyphenylene sulfide, polyacrylate, polymethacrylate, polyacrylate, epoxy resin, and silicone resin, and the like.

Regarding drying the coated film, heating and drying may be carried out by placing a substrate casted the solution on a heating plate, heating and drying may be carried out by placing a support body casted the solution in a heated drying oven, drying may be carried out by blowing warm gas such as air and nitrogen which is heated onto a coated film, or drying may be carried out by using a process combining the above. The temperature when drying is preferably 10° C. to 250° C., more preferably 20° C. to 220° C., and particularly preferably 30° C. to 200° C. and is selected in consideration of the characteristics of the varnish, the film thickness, and the heat resistance of the substrate. In addition, a coated film may be dried by setting multi-stage drying temperatures with two or more types of temperature settings. It is possible to select the time of drying the coated film from conditions in consideration of the boiling point of the varnish solvent, the thickness of the film, and the processing conditions. Hereby, a film is formed on a support body.

Subsequently, a UV irradiation step is performed with respect to the obtained film and the photocurable compound (B) is cured. In addition, the UV irradiation step may include sterilization. The irradiation light is not particularly limited as long as it is possible to impart energy which causes a radical reaction or ionic reaction by the photo-curing initiator (C) being irradiated with light. As the light source, it is possible to use rays with a wavelength of 400 nm or less, for example, a low pressure mercury lamp, a medium pressure mercury lamp, a high pressure mercury lamp, an ultra-high pressure mercury lamp, a chemical lamp, a black light lamp, a microwave excitation mercury lamp, a metal halide lamp, an i line, a G line, a KrF excimer laser light, and an ArF excimer laser light.

The irradiation strength to the film described above which is formed by the fluorine-containing cyclic olefin polymer composition is controlled according to each target product and is not particularly limited. For example, the light irradiation strength of the light wavelength region (although it is different according to the photo-curing initiator (C), for example, light of 300 to 420 nm is used) which is effective for activation of the photo-curing initiator (C) which will be described below is preferably 0.1 to 100 mW/cm$^2$. By setting the irradiation strength to be 0.1 mW/cm$^2$ or more, it is possible to reliably suppress the reaction time from being excessively long. On the other hand, by setting the irradiation strength to be 100 mW/cm$^2$ or less, it is possible to reliably suppress decreases in the cohesive force of the obtained cured matter, yellowing, or deterioration of the support body caused by heat radiated from the lamp heating the composition at the time of the polymerization of the composition.

The irradiation time of the light is controlled for each desired product and is not particularly limited; however, it is possible to set the accumulated light quantity which is represented as a product of the light irradiation strength in the light wavelength region and the light irradiation time to be, for example, 3 to 1000 mJ/cm$^2$. 5 to 500 mJ/cm$^2$ is more preferable and 10 to 300 mJ/cm$^2$ is particularly preferable. By setting the accumulated light quantity to be the lower limit value described or more, it is possible to make the generation of active species from the photopolymerization initiator (C) sufficient and to improve the characteristics of the obtained cured matter. On the other hand, it is possible to contribute to an improvement in the productivity by setting the accumulated light quantity to be the upper limit value described above or less. In addition, heating is also preferably used in order to promote the polymerization reaction in some cases. In addition, the temperature in a case of curing the curable resin by irradiation with light is generally preferably 0° C. to 150° C. and more preferably 0° C. to 60° C.

In a case of obtaining a substrate which is formed by a film or a single layer film in sheet form, for example, it is possible to produce a substrate by separating the film from the support body. The separation of the film from a support body may be performed by adhering a commercially available tape on an end section of the film and peeling by applying pressure thereto or may be performed by separating the film using the difference in surface tension between the support body surface and the contact surface of the film by bringing a liquid such as water or a solvent into contact with the contact interface of the film and the support body.

In a case of obtaining a substrate by forming an coated film on another material, for example, it is possible to produce a substrate which is formed of the support body and a coated film which is formed by the fluorine-containing cyclic olefin polymer of the present embodiment by carrying out the steps up to the step of drying the coated film. In this case, the support body is particularly preferably selected from an organic material such as PET or an acryl resin or an inorganic material such as glass and silicon.

The thickness of the cured film which is obtained by film-forming a fluorine-containing cyclic olefin polymer composition on a support body, heating, and subsequently curing by irradiation with light is not particularly limited; however, 1 μm to 10 mm is preferable, 5 μm at to 1 mm is more preferable, and 10 μm to 0.5 mm is even more preferable. When in these ranges, it is possible to obtain an independent single layer film or a coated film. In addition, it is also possible to make the volume contraction small during photocuring and reliably suppress deformation of the substrate. In addition, these are favorable ranges, for example, from the point of view of producing medical instrument which is used for cell culturing such as a culture bag, a culture plate, and a culture petri dish. In addition, it is possible to set the thickness of the film to match the process of producing the equipment.

Furthermore, the medical instrument which uses the fluorine-containing cyclic olefin polymer composition according to the present embodiment may be provided with, for example, a substrate formed by a film or a single layer film having a convex-concave structure, which is formed by the fluorine-containing cyclic olefin polymer composition of the present embodiment and is formed on a surface on which cells are held or in contact, or a substrate which is formed and obtained by adhering a film or a single layer film in sheet form having a convex-concave structure is formed on another material with an adhesive agent, a pressure sensitive adhesive, or the like and is particularly preferably used as a result of realizing a water contact angle of 121° to 160°.

Regarding the size of the convex-concave structure, a pattern of which the distance between convexities is 40 nm to 90 μm is shaped and it is possible to set the water contact angle in the desired range by making the distance preferably 60 nm to 80 μm, particularly preferably 80 nm to 70 μm, and the shape is not particularly limited.

Here, the convex-concave structure may be formed by various types of methods such as screen printing, an embossing process, submicron imprinting, and nano imprinting.

In particular, when forming the convex-concave structure by an imprinting method, examples thereof include a solution casting method which applies varnish, which is the fluorine-containing cyclic olefin polymer composition exemplified in the description above, which is obtained by dissolving the fluorine-containing cyclic olefin polymer (A) represented by Formula (1), the photocurable compound (B), and the photo-curing initiator (C) in an organic solvent on various patterns of molds which are made of quartz, silicon, nickel, resist, and the like.

Firstly, the varnish is prepared by performing filtration by passing through a filter a solution which is obtained by dissolving the fluorine-containing cyclic olefin polymer (A) represented by Formula (1), the photocurable compound (B), and the photo-curing initiator (C) in an organic solvent in the same manner as the method exemplified in the description above.

Next, it is possible to obtain a substrate formed a convex-concave structure by transcription with a pattern of a mold, which is formed by bringing a solution (varnish) prepared by the fluorine-containing cyclic olefin polymer composition described above into contact with a pattern surface of the mold in which the convex-concave structure is formed, evaporating the solvent, carrying out UV irradiation, and carrying out the separation.

In detail, examples thereof include a method (1) which includes a step of applying a solution (varnish) composed of a fluorine-containing cyclic olefin polymer composition and an organic solvent on a mold surface having a fine pattern and a step of evaporating the solvent from the solution, and a method (2) which includes a step of applying a solution (varnish) composed of a fluorine-containing cyclic olefin polymer composition and an organic solvent on a support body (a substrate), a step of pressing the upper surface of the applied layer with the mold surface in which the fine pattern is formed, and a step of evaporating the solvent from the applied layer, and the like and in all of these methods, a substrate forming a convex-concave structure is obtained by separating via the UV irradiation step after bringing the mold into contact with the fluorine-containing cyclic olefin polymer composition. Here, in method (2), it is also possible to carry out the pressing with the mold after evaporating the solvent from the applied layer.

There is no particular limitation on the material of the mold in which a fine pattern is formed on a surface which is used for producing the substrate in which the convex-concave structure of the present embodiment is formed, the method for bringing the mold into contact with the varnish composed of the fluorine-containing cyclic olefin polymer composition, or the method for drying the coated film, and it is possible to perform the above in the same manner as the method for producing the substrate in which the convex-concave structure is formed by using the prepared varnish from the fluorine-containing cyclic olefin polymer described above dissolved in an organic solvent.

Subsequently, the photocurable compound (B) is cured by performing a UV irradiation step with respect to the fluorine-containing cyclic olefin polymer composition which is formed on the mold. In addition, the UV irradiation step may include sterilization. There is no particular limitation on any of the conditions such as the light source, the irradiation strength, the irradiation time, the temperature at the time of irradiation in the UV irradiation step and it is possible to perform the above in the same manner as the method for producing a substrate from the fluorine-containing cyclic olefin polymer composition described above.

In a case of obtaining a substrate which is formed by a film or a single layer film in sheet form, it is possible to produce a substrate by separating the film from the mold after the UV irradiation. The separation of the film from a support body may be performed by adhering a commercially available tape on an end section of the film and peeling by applying pressure thereto or may be performed the separation of the film by using the difference in surface tension between the surface of support body and the contact surface of the film by bringing a liquid such as water and a solvent into contact with the contact interface of the film and the support body.

In a case of obtaining a substrate in which a coated film in which a convex-concave structure is formed on another support body (a substrate) is formed, for example, the steps up to the step of drying the coated film which is applied on the support body are carried out, as a result, a fluorine-containing cyclic olefin polymer composition is applied on the support body. Subsequently, it is possible to produce a substrate in which the coated film having a convex-concave structure composed of the fluorine-containing cyclic olefin polymer composition of the present embodiment is formed on the support body by bringing the pattern surface of the mold into contact with the applied surface of the fluorine-containing cyclic olefin polymer composition, crimping as necessary, and carrying out UV irradiation and separation. In this case, the support body is particularly preferably selected from an organic material such as polyethylene terephthalate (PET) and an acryl resin or an inorganic material such as glass, silicon, and aluminum.

The pressure used when bringing the pattern surface of the mold into contact with the applied surface of the fluorine-containing cyclic olefin polymer composition is in the range of 0.01 to 5 MPa, preferably 0.05 to 4 MPa, and more preferably 0.1 to 3 MPa and UV irradiation may be carried out while UV irradiation may be carried out with crimping or UV irradiation may be carried out after crimping by using a crimping apparatus such as a laminator. Hereby, regardless of the shape or size of the pattern, it is possible to produce a substrate having a convex-concave structure for holding cells or contacting the cells, in which the pattern of the mold is transcribed with high precision.

The film thickness of the cured film which is obtained by film-forming a fluorine-containing cyclic olefin polymer composition on a support body, heating, and curing by irradiation with light after crimping as necessary is not particularly limited; however, 1 µm to 10 mm is preferable, 5 µm to 1 mm is more preferable, and 10 µm to 0.5 mm is even more preferable. When in these ranges, it is possible to obtain an independent single layer film or coated film on the support body. In addition, it is also possible to make the volume contraction small during photocuring and reliably suppress deformation of the substrate while transcribing the pattern with high precision. In addition, these are favorable ranges, for example, from the point of view of producing medical instrument which is used for cell culturing such as a culture bag, a culture plate, and a culture petri dish. Furthermore, it is possible to set the thickness of the film to match the process of producing equipment.

From a film or sheet which is produced from the fluorine-containing cyclic olefin polymer composition, it is possible to manufacture medical instrument in the form of, for example, a bag, a tube, or the like by a heat sealing method, a sealing method which uses an adhesive agent, or the like. In addition, it is also possible to manufacture medical instrument in a form in which the film or sheet of the present embodiment is adhered on a surface of the substrate on which cells are held or in contact in, for example, medical instrument such as a petri dish, multi-well plate, or flask produced with other material such as polystyrene, polyethylene, or metal.

Next, a cell culture method which uses the medical instrument according to the present embodiment will be described.

(Cell Culture Method)

The cell culture method according to the present embodiment is provided with a step of inoculating cells over the surface of the substrate of the medical instrument according to the present embodiment so as to be in contact with or held on the surface, a step of obtaining cultured cells by culturing the cells, and a step of causing the cultured cells to float from the surface by adding a buffer solution over the surface. Hereby, it is possible to separate the cultured cells from a substrate without damaging the cells and it is possible to realize cell culturing by which efficient proliferation is possible.

In the present embodiment, as a form of cell culturing, it is possible to culture floating cells in a standing state after inoculating the cells within the medical instrument. This is realized by a surface which comes into contact with or holds the cells of the substrate being formed of the fluorine-containing cyclic olefin polymer according to the present embodiment or the fluorine-containing cyclic olefin polymer composition and is particularly favorably realized in a case where the water contact angle on the surface is 70° to 160°. In addition, culturing may be carried out by applying vibration in consideration of the form or proliferation property of the cells, culturing may be carried out while flowing the culture solution, or culturing may be carried out while stirring, and there is no particular limitation. Among these, the culturing is favorably selected in consideration of the characteristics of the cells, the form of the apparatus, and the productivity. In any form, by culturing the cells in the medical instrument according to the present embodiment, it is possible to be proliferated the cells as forming a colony while suppressing attachment or adhesion of the cells to the culture apparatus.

As the culturing method, it is possible to carry out the cell culturing with a method, for example, such as standing culturing, rotating culturing, microcarrier culturing, gyratory culturing, spheroid culturing, gel inside culturing, three-dimensional carrier culturing, and pressurizing circulation culturing by using medical instrument in which the substrate according to the present embodiment is processed into a container according to the various types of culturing methods. Among these, the method is favorably selected in consideration of the cell characteristics, the culture form, or the productivity and one method may be used individually or two or more types may be used together.

The temperature in these various types of culturing methods is preferably 35° C. to 40° C., more preferably 36° C. to 38° C., and particularly preferably 36.5° C. to 37.5° C. In addition, the pressure is preferably 0.02 to 0.5 MPa, more preferably 0.05 to 0.3 MPa, and particularly preferably 0.08 to 0.2 MPa. Furthermore, the hydrogen ion index (pH) is preferably 8 to 6 and more preferably 7.5 to 6.5.

Examples of the sterilization method when using the medical instrument according to the present embodiment as culture apparatus include wet sterilization involving dipping in alcohol or the like, gas sterilization by ethylene oxide, ultraviolet sterilization, radiation sterilization, autoclave sterilization by high temperature and high pressure water vapor, dry heat sterilization which is used for things which are not allowed to touch vapor directly, filtration sterilization which is suitable for a substrate which includes components which are unstable when heated, and the like. Among these, the sterilization is favorably selected in consideration of the process compatibility within a range which does not inhibit the effects of the present invention and two or more types of sterilization methods may be used in combination.

In addition, it is possible to select the type of culture medium which is used for the culturing according to the characteristics of the cells and the culture form regardless of the form such as liquid, gel, or solid (powder) and examples thereof include a BME culture medium, an MEM culture medium, a DMEM culture medium, a 199 culture medium, an RPMI culture medium, a Ham's F10 culture medium, a Ham's F12 culture medium, an MCDB 104, 107, 131, 151, 170, and 202 culture media, an RITC 80-7 culture medium, an MCDB 153 culture medium, and the like. These may be used individually or may be used in a combination of two or more types and moreover, may be used in a combination with a blood serum which is derived from animals such as humans, dogs, rats, mice, birds, pigs, or cows.

Furthermore, for example, collagen such as laminin-5, laminin-511, and laminin-521, the fluorine-containing cyclic olefin polymer of the present embodiment, the fluorine-containing cyclic olefin polymer composition, or the like may be applied on an inner wall of the substrate of the present embodiment or a part of a surface or all the surface which comes into contact with or holds the cells to be used according to the purpose of the cell culturing within a range which does not inhibit the effects of the present invention. The above may be used individually or in a combination of two or more types. In addition, in the present embodiment, it is possible to select a culture solution of cells or a buffer solution according to the type of the cells or the application of the cultured cell and a fluorescent pigment or cell hardening reagent may also be freely selected.

Furthermore, it is sufficient if the buffer solution which is used when culturing or separating cultured cells from a substrate by floating does not change the hydrogen ion index (pH) in the system in the process of the cells proliferating and, generally, a single buffer solution may be used such as, for example, a phosphoric acid buffer solution, phosphate buffered physiological saline, a hydrochloric acid buffer solution, an acetate buffer solution, a citric acid buffer solution, a boric acid buffer solution, a tartaric buffer solution, a tris buffer solution, a tris-hydrochloric acid buffer solution, an ethylene diamine tetraacetic acid buffer solution, a tris EDTA buffer solution, a tris acetate EDTA buffer solution, a tris boric acid EDTA buffer solution, a concentrated SSC buffer solution, a concentrated SSPE buffer solution, a sodium citrate buffer solution, a bicarbonate carbonate buffer solution, a sodium borate buffer solution, a maleic buffer solution, a CABS buffer solution, a piperidine buffer solution, a glycine buffer solution, a malic acid buffer solution, a formic acid buffer solution, a succinic acid buffer solution, an acetate buffer solution, a propionic acid buffer solution, a piperazine buffer solution, a pyridine buffer solution, a cacodylic acid buffer solution, a MES buffer solution, a histidine buffer solution, an ethanol amine buffer solution, an ADA buffer solution, a carbonate buffer solution, an ACES buffer solution, a PIPES buffer solution, an imidazole buffer solution, a bis-trispropane buffer solution, a BES buffer solution, a MOPS buffer solution, a HEPES buffer solution, a TES buffer solution, a MOPSO buffer solution, a MOBS buffer solution, a DIPSO buffer solution, a TAPSO buffer solution, a TEA buffer solution, a pyrophosphoric acid buffer solution, a HEPPSO buffer solution, a POPSO buffer solution, a tricine buffer solution, a hydrazine buffer solution, a glycylglycine buffer solution, an EPPS buffer solution, a bicine buffer solution, a HEPBS buffer solution, a TAPS buffer solution, an AMPD buffer solution, a TABS buffer solution, an AMPSO buffer solution, a taurine buffer solution, a CHES buffer solution, a glycine buffer solution, an ammonium hydroxide buffer solution, a CAPSO buffer solution, a methylamine buffer solution, a CAPS buffer solution, and the like individually, or a buffer solution which contains enzymes such as trypsin, pepsin, rennet, chymotrypsin, elastase, NADPH dehydrogenase, or NADH dehydrogenase may be used, A buffer solution containing a phosphoric acid buffer solution, phosphate buffered physiological saline, a hydrochloric acid buffer solution, an acetate buffer solution, a citric acid buffer solution, a boric acid buffer solution, a tartaric buffer solution, a tris buffer solution, a tris-hydrochloric acid buffer solution, an ethylenediaminetetraacetic acid buffer solution, a tris EDTA buffer solution, a tris acetate EDTA buffer solution, a tris boric acid EDTA buffer solution, a concentrated SSC buffer solution, a concentrated SSPE buffer solution, a sodium citrate buffer solution, a bicarbonate carbonate buffer solution, a sodium borate buffer solution, a maleic buffer solution, and the like individually may be preferably used or a buffer solution which contains enzymes such as trypsin, pepsin, rennet, chymotrypsin, elastase, NADPH dehydrogenase, or NADH dehydrogenase may be used.

More preferably, a phosphoric acid buffer solution, phosphate buffered physiological saline, a tris-hydrochloric acid buffer solution, an ethylenediaminetetraacetic acid buffer solution, a tris EDTA buffer solution, a tris acetate EDTA buffer solution, a tris boric acid EDTA buffer solution, a concentrated SSC buffer solution, a concentrated SSPE buffer solution, a sodium citrate buffer solution, a bicarbonate carbonate buffer solution, a sodium borate buffer solution, and the like may be used individually or a buffer solution which contains enzymes such as trypsin, pepsin, rennet, chymotrypsin, elastase, NADPH dehydrogenase, or NADH dehydrogenase may be used.

As a result of intensive research, the present inventors discovered a phenomenon that cells are separated from a substrate in a naturally floating state, for example, when a buffer solution such as phosphate buffered physiological saline is added thereto, for example, in the process of culturing a mouse embryo fibroblast and taking the cell for inspection, by using the culture apparatus of the present embodiment. In other words, according to the present embodiment, by carrying out cell culturing using culture apparatus which is formed of a specific fluorine-containing cyclic olefin polymer or a fluorine-containing cyclic olefin polymer composition, it is possible to realize an excellent cell culture method in which cells proliferate while floating and forming a colony and the proliferated cells are able to be floated and separated from the substrate without damaging the cells.

Here, the present invention is not limited to the embodiment described above and alterations, improvements, and the like in a range in which it is possible to achieve the object of the present invention are included in the present invention.

EXAMPLES

Description will be given below of the present invention in the Examples; however, the present invention is not limited by these examples. Here, in the Examples, a polymer analysis value measuring method, a method for treating cells, a culture apparatus sterilization method, and a culture evaluation method will be described below.

[Weight Average Molecular Weight (Mw) and Molecular Weight Distribution (Mw/Mn)]

Using gel permeation chromatography (GPC) under the following conditions, the weight average molecular weight (Mw) and the number average molecular weight (Mn) of the polymer which is dissolved in tetrahydrofuran (THF) or trifluoromethyl benzene (TFT) were measured by calibrating the molecular weight according to a polystyrene standard.

Detection device: RI-2031 and 875-UV manufactured by JASCO Corporation or Model 270 manufactured by Viscotec, series circuit column: Shodex K-806M, 804, 803, and 802.5, column temperature: 40° C., flow amount: 1.0 ml/min, sample concentration: 3.0 to 9.0 mg/ml

[Glass Transition Temperature]

Using DSC-50 manufactured by Shimadzu Corporation, the measuring sample was measured by heating at an increasing temperature speed of 10° C./min under a nitrogen atmosphere.

[Water Contact Angle Measurement]

Using a solid content surface energy analysis apparatus CA-XE model manufactured by Kyowa Interface Science Co., Ltd., on the basis of JIS R3257 (a wettability test method of a substrate glass surface), water droplets of 2 μl were dripped onto a substrate surface and the contact angle was measured within a minute after the water droplets came into contact with the substrate surface by a sessile drop method.

[UV Curing]

The coated film was cured by irradiation with LED light with a wavelength at 365 nm using a UV irradiation apparatus manufactured by CCS Inc. as light source or 375 nm LED light using a UV type imprint apparatus manufactured by Engineering System Corporation.

[Cell Type and Culture Solution]

Using a mouse embryo fibroblast (abbreviated below as BALB/3T3 cells), all the subculture and cell proliferation property tests were performed in a solution (also referred to below as a BALB/3T3 cell solution) which included 10% calf bovine serum (CBS), high glucose, and a D-MEM culture medium (containing L-glutamine, phenol red, and sodium pyruvate).

[Thawing Cells]

A frozen cell suspension was thawed by dipping in a 37° C. water bath, 10% calf serum D-MEM culture medium which was cooled on ice was added to the thawed cell suspension, and then centrifugal separation was carried out. After the centrifugal separation, removing the supernatant liquid and loosening the cell aggregation by tapping, the 10% calf serum D-MEM culture medium which was kept in the 37° C. water bath was added. After counting the number of the cells with a hemocytometer, preparing the cell suspension using the 10% calf serum D-MEM culture medium which was kept in the 37° C. water bath and inoculating the cells in a culture flask, culturing was carried out in a humidifying incubator.

[Subculture of Cells]

The culture flask was taken out from the humidifying incubator, the culture medium was removed by an aspirator, Dulbecco PBS (−) which was kept in the 37° C. water bath was added, and the supernatant liquid was removed by an aspirator. After performing the same operation again, a 0.025 w/v % trypsin-EDTA solution which was kept in the 37° C. water bath was added and left to stand in the humidifying incubator, then the 10% calf serum D-MEM culture medium was added, the peeled off cells were collected and transferred into a centrifuge tube, the supernatant liquid was removed by carrying out centrifugal separation, the cell aggregation was loosened by tapping, and then the 10% calf serum D-MEM culture medium was added. After counting the number of the cells with a hemocytometer, the cell suspension was prepared using the 10% calf serum D-MEM culture medium, the cells were inoculated in a culture flask, and culturing was carried out in a humidifying incubator. In the cell proliferation property evaluation described in the Examples, cells with the subculture number of 3's to 20's were used.

[Method for Sterilizing Cell Culture Apparatus]

The culture film with a circular shape which was cut out to a diameter of 15 mm was placed in a TOPS multi-well plate (manufactured by Corning Incorporated) hole section, and dipping was carried out for 40 minutes to 1 hour by adding a 70% ethanol water solution thereto, and then the 70% ethanol water solution was removed and dipping was carried out in Dulbecco PBS (−) for 15 minutes to 40 minutes. Next, the PBS (−) was removed, the culture apparatus was turned over, the same operation was performed, and a sterilization process was carried out on the front and rear surfaces of the culture apparatus. After completing the sterilization process, drying was carried out in a clean bench overnight.

[Preparation of Cell Suspension]

The BALB/3T3 cells which are in approximately 60% confluent state in a 25 cm$^2$ culture flask were peeled off by carrying out a treatment with 0.025 w/v % trypsin-EDTA in the same manner as the subculture operation of the cells described above. The number of the cells was counted with a hemocytometer and 7500 cells/mL of the cell suspension was prepared using the 10% calf serum D-MEM culture medium.

[Evaluation of Cell Proliferation Property]

The TCPS multi-well plates after 1, 3, and 7 days passed as of starting the culture were taken out from the humidifying incubator and the culture medium was removed, a mixed solution of 10% WST-8 (Cell Counting Kit-8)/10% calf serum D-MEM culture medium was added, and incubating was carried out in a humidifying incubator for 3 hours. After that, the culture medium 200 μl was transferred to 96-well plate and the absorbency of the wavelength of 450 nm was measured by a plate reader (SPECTRA max PLUS 384, manufactured by Molecular Devices LCC.). The cell proliferation property of each culture apparatus was confirmed according to the change in the absorbency over time.
[Significance Test]

For various types of culture apparatus, 9 samples in which cells were inoculated were prepared and cultured, the measurement results of the absorbency were analyzed according to the numeric value by Prism 6 for Windows (register trade mark) 6.01 (manufactured by MDF Co., Ltd.), the average value of the results was calculated as the absorbency, and the standard deviation was given a reference numeral of ± and was the range of variation.
[Fluorescence Microscope Observation]

The culture medium was removed from the container in which the cell culturing was carried out for 7 days, a 4% glutaraldehyde/phosphoric acid buffer solution was added and left to stand for 1 hour, and then the 4% glutaraldehyde/phosphoric acid buffer solution was removed. After that, cleansing was carried out using sterilizing water, cell nuclei and cytoskeletal proteins were dyed using an Image-iT Fixation/Permeabilization kit (manufactured by Life Sciences Corporation), and a sample which was used for fluorescence microscope observation was prepared. An all in one fluorescence microscope BZ-X700 (manufactured by Keyence Corporation) was used for the fluorescence microscope observation.

Production Example 1

Polymer 1

A tetrahydrofuran solution of $Mo(N-2,6-Pr^i_2C_6H_3)(CHCMe_2Ph)(OBu^t)_2$ (50 mg) was added to a tetrahydrofuran solution of 5,5,6-trifluoro-6-(trifluoromethyl)bicyclo[2.2.1]hepto-2-ene (100 g) and 1-hexene (0.268 g) and ring opening metathesis polymerization was performed at 70° C. A hydrogenating reaction was carried out on the olefin portion of the obtained polymer at 160° C. using palladium alumina (5 g) and a tetrahydrofuran solution of poly(1,1,2-trifluoro-2-trifluoromethyl-3,5-cyclopentylene ethylene) was obtained. The solution was filtered under pressure by a filter with a pore diameter of 5 μm and a solution from which palladium alumina is removed was added to methanol, a white polymer was filtered, separated, and dried, and 99 g of polymer 1 was obtained. The obtained polymer 1 contains a repeating structure unit represented by Formula (1) described above. In addition, the hydrogenating ratio was 100%, the weight average molecular weight (Mw) was 83000, the molecular weight distribution (Mw/Mn) was 1.73, and the glass transition temperature was 109° C.

Production Example 2

Culture Film 1

The polymer 1 which was synthesized in Production Example 1 was dissolved in methylisobutyl ketone at a concentration of 30 mass %, the solution was filtered under pressure by a filter with a pore diameter of 1 μm and then filtered by a filter of 0.1 μm to prepare a methylisobutyl ketone solution of the polymer 1. Subsequently, the methylisobutyl ketone solution of the polymer 1 was applied on a glass substrate and evenly applied using an applicator, and then a film with a thickness of 60 μm was produced by drying at 140° C. for 60 minutes and separating. The water contact angle of the film was 93.6° after 15 seconds. Furthermore, the water contact angle was 88.1° after 10 minutes passed and change was not seen in the time until the water droplets disappeared.

Production Example 3

Culture Film 2

The methylisobutyl ketone solution of the polymer 1 which was prepared in Production Example 2 was evenly applied on a PET film (Lumirror, Toray Industries, Inc.) which was an application substrate using a bar coater, dried at 100° C. for 20 minutes and left to cool to room temperature, and the culture film 2 with an coated film thickness of 5 μm was produced. The water contact angle of the film was 93.7° after 15 seconds. Furthermore, the water contact angle was 87.7° after 10 minutes passed and change was not seen in the time until the water droplets disappeared.

Production Example 4

Culture Film 3

The culture film 3 with a coated film thickness of 5 μm was produced by the same method as Production Example 3 apart from changing the coated substrate to an acryl film (Acryplen, Mitsubishi Rayon Co., Ltd.) and the drying conditions after applying to 90° C. and 40 minutes. The water contact angle of the film was 94.1° after 15 seconds. Furthermore, the water contact angle was 88.0° after 10 minutes passed and change was not seen in the time until the water droplets disappeared.

Production Example 5

Culture Film 4

A solution in which 7.5 g [(A)/(B)=80/20] of mixed matter with a mass ratio 9/1 of 3-ethyl-3{[(3-ethyl oxetan-3-yl)methoxy]methyl}oxetane and 1,7-octadiene diepoxide as the photocurable compound (B) and 0.4 g of cationic photoinitiator (Adeka optomer SP-172, produced by Adeka Corporation) as the photo-curing initiator (C) was added to 100 g of methylisobutyl ketone solution in which the polymer 1 which is the fluorine-containing cyclic olefin polymer (A) which was synthesized in Production Example 1 was dissolved at 30 mass % concentration was prepared, filtered under pressure by a filter with a pore diameter of 1 μm, and subsequently filtered by a 0.1 μm filter, and then the methylisobutyl ketone solution of the polymer 1, the photocurable compound, and the photo-curing initiator was prepared. Subsequently, application was carried out on a PET film (Lumirror, Toray Industries, Inc.) which was an coated substrate, application was evenly carried out using a bar coater, drying was carried out at 100° C. for 10 minutes and, after being left to cool to room temperature, a hardening resin was cured by carrying out UV irradiation with a light amount of 200 mJ/cm² and the culture film 4 with a coated film thickness of 5 μm was produced. The water contact angle of the applied surface was 88.1° after 15 seconds. Furthermore, the water contact angle was 84.9° after 10 minutes passed and change was not seen in the time until the water droplets disappeared.

Production Example 6

Culture Film 5

The culture film 5 with a coated film thickness of 5 μm was produced by the same method as Production Example 5 apart from changing the mass ratio of the polymer 1 which was the fluorine-containing cyclic olefin polymer (A) and mixed matter with a mass ratio 9/1 of 3-ethyl-3{[(3-ethyl oxetan-3-yl)methoxy]methyl}oxetane and 1,7-octadiene diepoxide which was the photocurable compound (B) to [(A)/(B)=60/40]. The water contact angle of the applied surface was 84.2° after 15 seconds. Furthermore, the water contact angle was 81.3° after 10 minutes passed and change was not seen in the time until the water droplets disappeared.

Production Example 7

Culture Film 6

The culture film 6 with a coated film thickness of 5 μm was produced by the same method as Production Example 6 apart from changing the coated substrate to an acryl film (Acryplen, Mitsubishi Rayon Co., Ltd.) and the drying conditions after application to 90° C. and 40 minutes. The water contact angle of the film was 84.3° after 15 seconds. Furthermore, the water contact angle was 81.0° after 10 minutes passed and change was not seen in the time until the water droplets disappeared.

Production Example 8

Culture Film 7

0.5 mass % of Smilizer GP (produced by Sumitomo Chemical Co., Ltd.) was added to the polymer 1 which was synthesized in Production Example 1 as a heat resistant antioxidant and, after pelletizing by a pelletizer, the temperature of a heating and kneading section was set to be 260° C. and the temperature of the mold to be 90° C. using a miniature injection molding apparatus Micro-1 manufactured by Meihokagaku, and the culture film 7 with a diameter of 20 mm and a thickness of 3 mm was produced under conditions of an injection speed of 20 mm/sec and an injection pressure of 40 MPa. The water contact angle of the substrate surface was 94.0° after 15 seconds. Furthermore, the water contact angle was 88.4° after 10 minutes passed and change was not seen in the time until the water droplets disappeared.

Example 1

After the culture film 1 which was produced in Production Example 2 and already sterilized was placed on the bottom surface of the hole section of a 24-well TCPS multi-well plate and fixed by adhering to an O-ring (inner diameter of 11 mm) made of SUS with sterilizing grease (produced by Dow Corning Toray Co., Ltd.), a BALB/3T3 cell solution (1 mL) was inoculated on the culture film 1. The same operation was carried out 9 times and 9 samples were prepared as the number of samples.

After that, a lid was put thereon and the samples were moved to a humidifying incubator and culturing was started in sterilized air with an inside temperature at 37° C. and a carbonic acid gas concentration at 5%.

In the evaluation of the cell proliferation property by the WST-8 method, the absorbency was 0.10±0.02 after 1 day passed, 0.35±0.08 after 3 days passed, and 0.73±0.24 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 2

The culture film 2 which was produced in Production Example 3 and already sterilized was fixed on a 24-well TCPS multi-well plate in the same manner as Example 1 and a thawed BALB/3T3 cell solution (1 mL) was inoculated thereon. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.11±0.02 after 1 day passed, 0.36±0.05 after 3 days passed, and 0.78±0.13 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 3

The culture film 3 which was produced in Production Example 4 and already sterilized was fixed on a 24-well TCPS multi-well plate in the same manner as Example 1 and a thawed BALB/3T3 cell solution (1 mL) was inoculated thereon. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.11±0.04 after 1 day passed, 0.38±0.04 after 3 days passed, and 0.83±0.11 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 4

The culture film 4 which was produced in Production Example 5 and already sterilized was fixed on a 24-well TCPS multi-well plate in the same manner as Example 1 and a thawed BALB/3T3 cell solution (1 mL) was inoculated thereon. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.11±0.03 after 1 day passed, 0.23±0.04 after 3 days passed, and 0.51±0.11 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 5

The culture film 5 which was produced in Production Example 6 and already sterilized was fixed on a 24-well TCPS multi-well plate in the same manner as Example 1 and a thawed BALB/3T3 cell solution (1 mL) was inoculated thereon. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.11±0.02 after 1 day passed, 0.27±0.04 after 3 days passed, and 0.55±0.18 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 6

The culture film 6 which was produced in Production Example 7 and already sterilized was fixed on a 24-well TCPS multi-well plate in the same manner as Example 1 and a thawed BALB/3T3 cell solution (1 mL) was inoculated thereon. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.11±0.04 after 1 day passed, 0.23±0.02 after 3 days passed, and 0.53±0.13 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 7

The culture film 7 which was produced in Production Example 8 and already sterilized was placed on the bottom surface of the hole section of a 24-well TCPS multi-well plate and fixed by adhering to an O-ring (inner diameter of 16 mm) made of SUS with sterilizing grease (produced by Dow Corning Toray Co., Ltd.), after which a thawed BALB/3T3 cell solution (1 mL) was inoculated on the culture film 7. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.11±0.05 after 1 day passed, 0.42±0.15 after 3 days passed, and 0.96±0.06 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 8

97 g of polymer 2 was obtained using the same method as Production Example 1 except that the type of fluorine-containing cyclic olefin monomer was changed to 5,6-difluoro-5-pentafluoroethyl-6-trifluoromethyl bicyclo[2.2.1]hept-2-ene. The obtained polymer 2 contained a repeating structure unit represented by Formula (1) described above. In addition, the hydrogenation rate was 100%, the weight average molecular weight (Mw) was 91000, the molecular weight distribution (Mw/Mn) was 1.93, and the glass transition temperature was 104° C.

Next, the culture film 8 with a thickness of 55 μm was prepared according to the same method as Production Example 2. The water contact angle of the film was 101.6° at 15 seconds. Furthermore, the water contact angle was 99.7° after 10 minutes passed and changes were not seen in the time up to when the water droplets were lost.

For the culturing of the BALB/3T3 cells carried out in the same manner as in Example 1 using the culture film 8, in the evaluation of the cell proliferation property by the TWT-8 method, the absorbency was 0.10±0.01 after 1 day passed, 0.33±0.05 after 3 days passed, and 0.74±0.17 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 9

The polymer 2 produced in Example 8 which is the fluorine-containing cyclic olefin polymer (A), and a mixture with a mass ratio of 9/1 of 3-ethyl-3{[(3-ethyl oxetan-3-yl)methoxy]methyl}oxetane and 1,7-octadiene diepoxide as the photocurable compound (B) were mixed with the same method as Production Example 5 and a composition with [mass ratio (A)/(B)=80/20] was prepared. Next, the culture film 9 was produced by applying a PET film (Lumirror, by Dow Corning Toray Co., Ltd). The water contact angle of the film was 95.3° at 15 seconds. Furthermore, water contact angle was 94.9° after 10 minutes passed and changes were not seen in the time up to when the water droplets were lost.

For the culturing of the BALB/3T3 cells carried out in the same manner as in Example 1 using the culture film 9, in the evaluation of the cell proliferation property by the TWT-8 method, the absorbency was 0.10±0.01 after 1 day passed, 0.25±0.07 after 3 days passed, and 0.60±0.13 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Example 10

98 g of polymer 3 was obtained using the same method as Production Example 1 except that the type of fluorine-containing cyclic olefin monomer was changed to 5,6-difluoro-5-heptafluoro-iso-propyl-6-trifluoromethylbicyclo[2.2.1]hept-2-ene. The obtained polymer 3 contained a repeating structure unit represented by Formula (1) described above. In addition, the hydrogenation rate was 100%, the weight average molecular weight (Mw) was 142000, the molecular weight distribution (Mw/Mn) was 1.40, and the glass transition temperature was 137° C.

Next, the culture film 10 with a thickness of 58 μm was produced according to the same method as Production Example 2. The water contact angle of the film was 103.9° at 15 seconds. Furthermore, the water contact angle was 102.2° after 10 minutes passed and changes were not seen in the time up to when the water droplets were lost.

For the culturing of the BALB/3T3 cells carried out in the same manner as in Example 1 using the culture film 10, in the evaluation of the cell proliferation property by the TWT-8 method, the absorbency was 0.11±0.03 after 1 day passed, 0.32±0.03 after 3 days passed, and 0.79±0.21 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when phosphate buffered physiological saline was added thereto.

Production Example 9

Culture Film 13

The polymer 1 which was synthesized in Production Example 1 was dissolved in methylisobutyl ketone at a concentration of 30 mass %, the solution was filtered under pressure by a filter with a pore diameter of 1 μm and then filtered by a filter of 0.1 μm to prepare a methylisobutyl ketone solution of the polymer 1. Subsequently, the methylisobutyl ketone solution of the polymer 1 was applied on a 4 cm×4 cm sized nickel mold having hole shapes with a diameter of 150 nm and a pitch of 250 nm and evenly applied using an applicator, and then the culture film 13 with pillar shape and a thickness of 50 μm was produced by drying at 140° C. for 60 minutes and separating. The water contact angle of the culture film 13 was 147.0° (after 15 seconds).

Production Example 10

Culture Film 14

The methylisobutyl ketone solution of the polymer 1 used in Production Example 9 was applied on a 5 cm×5 cm sized silicon mold with lines and spaces with a line width of 200 nm and a pitch of 400 nm densely arrayed vertically and horizontally at 2 μm periods and evenly applied using an applicator, and then the culture film 14 with a hole shape with a thickness of 50 μm was produced by drying at 140° C. for 60 minutes and separating. The water contact angle of the culture film 14 (after 15 seconds passed) was 136.0°.

Production Example 11

Culture Film 15

The methylisobutyl ketone solution of the polymer 1 used in Production Example 9 was applied on a 4 cm×4 cm sized nickel mold having pillar shapes with a diameter of 150 nm and a pitch of 250 nm and evenly applied using an applicator, and then the culture film 15 with a hole shape and a thickness of 50 μm was produced by drying at 140° C. for 60 minutes and separating. The water contact angle of the culture film 15 was 124.3° (after 15 seconds).

Production Example 12

Culture Film 16

The methylisobutyl ketone solution of the polymer 1 used in Production Example 9 was applied on a 4 cm×4 cm sized quartz mold having dome shapes with a diameter of 25 μm and evenly applied using an applicator, and then the culture film 16 having a reverse pattern with a dome shape and a thickness of 60 μm was produced by drying at 140° C. for 60 minutes and separating. The water contact angle of the culture film 16 was 127.3° (after 15 seconds).

Production Example 13

Culture Film 17

A solution was prepared in which 20 g [(A)/(B)=60/40] of a mixture with a mass ratio of 9/1 of 3-ethyl-3{[(3-ethyl-oxetan-3-yl)methoxy]methyl}oxetane as the photocurable compound (B) and 1,7-octadiene diepoxide and 0.8 g as a photo-curing initiator (C) (Adekaoptomer SP-172, produced by ADEKA Corporation) were added to 100 g of methyl isobutyl ketone solution in which the polymer 1 synthesized in Production Example 1 was dissolved at 30 mass % concentration, the solution was filtered under pressure by a filter with a pore diameter of 1 μm, and then filtered by a filter of 0.1 μm to prepare photocurable composition 1. Next, after evenly applying the photocurable composition 1 using an applicator on a quartz mold using the Production Example 12, drying was carried out for 30 minutes at 140° C., the resultant was irradiated with UV light with a wavelength at 365 nm from the rear surface of the application surface with a total light quantity of 200 mJ/cm², then, the culture film 17 with a dome shape with a thickness of 60 μm was prepared by carrying out separation from the mold. The water contact angle of the culture film 17 was 129.5° (after 15 seconds).

Example 11

The culture film 13 which was produced in Production Example 9 was sterilized and a pattern surface was placed on the bottom surface of a hole section of a 24-well TCPS multi-well plate and fixed by adhering to an O-ring (inner diameter of 11 mm) made of SUS with sterilizing grease (produced by Dow Corning Toray Co., Ltd.), after which a BALB/3T3 cell solution (1 mL) was inoculated on a pattern surface of the culture film 13. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.10±0.03 after 1 day passed, 0.33±0.06 after 3 days passed, and 0.68±0.09 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 12

The culture film 14 which was produced in Production Example 10 was sterilized and was fixed on a 24-well TCPS multi-well plate with the same method as Example 1 and a thawed BALB/3T3 cell solution (1 mL) was inoculated on the pattern surface of the culture film 14. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.10±0.01 after 1 day passed, 0.32±0.06 after 3 days passed, and 0.67±0.10 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 13

The culture film 15 which was produced in Production Example 11 was sterilized and fixed on a 24-well TCPS multi-well plate by the same method as Example 1, and a thawed BALB/3T3 cell solution (1 mL) was inoculated on the pattern surface of the culture film 15. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.10±0.02 after 1 day passed, 0.34±0.03 after 3 days passed, and 0.70±0.09 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 14

The culture film 16 which was produced in Production Example 12 was sterilized and fixed on a 24-well TCPS multi-well plate by the same method as Example 1, and a thawed BALB/3T3 cell solution (1 mL) was inoculated on a pattern surface of the culture film 16. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.09±0.02 after 1 day passed, 0.32±0.03 after 3 days passed, and 0.66±0.08 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 15

The culture film 17 which was produced in Production Example 13 was sterilized and fixed on a 24-well TCPS multi-well plate by the same method as Example 1, and a thawed BALB/3T3 cell solution (1 mL) was inoculated on a pattern surface of the culture film 17. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.10±0.04 after 1 day passed, 0.26±0.02 after 3 days passed, and 0.52±0.12 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 16

Using the polymer 2 produced in Example 8, the culture film 18 with a pillar shape with a thickness of 55 μm was produced using the same method as Production Example 9. The water contact angle of the culture film 18 was 150.5° (after 15 seconds).

For the culturing of the BALB/3T3 cells carried out with the same method as in Example 1 using the culture film 18, in the evaluation of the cell proliferation property by the TWT-8 method, the absorbency was 0.10±0.03 after 1 day passed, 0.32±0.03 after 3 days passed, and 0.72±0.10 after 7 days passed. The absorbance increased in a straight line over the passing days and change was not seen in the proliferation property even after 7 days passed. In addition, when observing the cells which were cultured for 7 days using the microscope, the cells proliferated colony in a state of forming a colony in the thickness direction and floated in a state of keeping a colony form when phosphate buffered physiological saline was added thereto.

Example 17

The culture film 19 with a hole shape and a thickness of 58 μm was produced using the same method as Production Example 9 except that the mold was changed to a nickel mold with a pillar shape used in Production Example 11, using the polymer 3 produced in Example 10. The water contact angle of the culture film 19 was 130.3° (after 15 seconds).

For the culturing of the BALB/3T3 cells carried out with the same method as in Example 1 using the culture film 19, in the evaluation of the cell proliferation property by the TWT-8 method, the absorbency was 0.09±0.02 after 1 day passed, 0.32±0.04 after 3 days passed, and 0.78±0.19 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 18

A film with a thickness of 50 μm produced from the polymer 1 synthesized in Production Example 1 was placed to cover the pattern surface of a nickel mold with a hole shape used in Production Example 9, heated to 150° C., thermo-compression bonded at 10 MPa and held for 5 seconds as it was. After cooling to 50° C., the resultant was separated from the mold and the culture film 20 with a pillar shape was produced. The water contact angle of the culture film 20 was 148.1° (after 15 seconds).

For the culturing of the BALB/3T3 cells carried out with the same method as in Example 1 using the culture film 20, in the evaluation of the cell proliferation property by the TWT-8 method, the absorbency was 0.11±0.03 after 1 day passed, 0.39±0.04 after 3 days passed, and 0.81±0.11 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 19

After spin coating the photocurable composition 1 [(A)/(B)=60/40] prepared in Production Example 13 on a PET film and heating for 1 minute at 100° C., the PET film was covered such that the pattern surface of the nickel mold with a hole shape used in Production Example 9 and the application surface of the photocurable composition 1 come into contact, and UV light with a wavelength at 375 nm was irradiated with a total light quantity of 200 mJ/cm$^2$ while pressing at a pressure of 0.3 MPa. Next, the PET film was peeled off from the nickel mold to produce the culture film 21 formed with a pillar shape on the surface of the PET film. The water contact angle of the culture film 21 was 146.9° (after 15 seconds).

For the culturing of the BALB/3T3 cells carried out with the same method as in Example 1 using the culture film 21, in the evaluation of the cell proliferation property by the TWT-8 method, the absorbency was 0.11±0.02 after 1 day passed, 0.26±0.03 after 3 days passed, and 0.53±0.10 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

Example 20

The cell type was changed to human skin fibroblasts (referred to below simply as Hs-68 cells), cell thawing and subculturing were carried out, and a suspension was prepared using the same method as mouse embryo fibroblasts, and a cell suspension of 7500 cells/mL was prepared with a 10% calf serum D-MEM culture medium.

Next, using the sterilized culture film 1 produced in Production Example 2, a thawed Hs-68 cell solution (1 mL) was inoculated according to the same method as Example 1. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.34±0.07 after 1 day passed, 1.55±0.10 after 3 days passed, and 4.27±0.16 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when trypsin-containing phosphate buffered physiological saline was added thereto.

When evaluating the drug-metabolizing enzymes activity of these cultured cells in NADPH dehydrogenase, it was understood that almost 100% had drug metabolizing system enzyme activity similar to living cells. Furthermore, when the autofluorescence was observed, it was confirmed that 100% of the cultured cells were living cells in the same manner.

Example 21

Using the sterilized culture film 5 produced in Production Example 6, a thawed Hs-68 cell solution (1 mL) was inoculated according to the same method as Example 20. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.31±0.03 after 1 day passed, 1.49±0.09 after 3 days passed, and 3.77±0.19 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when trypsin-containing phosphate buffered physiological saline was added thereto.

When evaluating the drug-metabolizing enzymes activity of these cultured cells in NADPH dehydrogenase, it was understood that almost 100% had drug metabolizing system enzyme activity similar to living cells. Furthermore, when the autofluorescence was observed, it was confirmed that 100% of the cultured cells were living cells in the same manner.

Example 22

Next, using the sterilized culture film 10 produced in Production Example 10, a thawed Hs-68 cell solution (1 mL) was inoculated according to the same method as Example 20. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.33±0.04 after 1 day passed, 1.53±0.05 after 3 days passed, and 4.17±0.11 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when trypsin-containing phosphate buffered physiological saline was added thereto.

When evaluating the drug-metabolizing enzymes activity of these cultured cells in NADPH dehydrogenase, it was understood that almost 100% had drug metabolizing system enzyme activity similar to living cells. Furthermore, when the autofluorescence was observed, it was confirmed that 100% of the cultured cells were living cells in the same manner.

Example 23

The bottom surface of a recess section of a 6 hole TCPS multi-well plate (manufactured by Corning) was cut out, the film 1 produced in Production Example 2 was adhered to the recess bottom section of all 6 holes, and a cell culturing container was produced and subjected to a sterilization process with ethanol.

Next, a thawed Hs-68 cell solution was inoculated according to the same method as Example 20 except that the amount of the cell solution was changed to 10 mL. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.52±0.03 after 1 day passed, 1.70±0.03 after 3 days passed, and 4.35±0.09 after 7 days passed. The absorbance increased in a straight line over the passing days and change was not seen in the proliferation property even after 7 days passed. In addition, when observing the cells which were cultured for 7 days using the microscope, the cells proliferated in sheet form in a state of forming a colony in the thickness direction and floated in a state of keeping a sheet form when trypsin-containing phosphate buffered physiological saline was added thereto.

Figure 2:
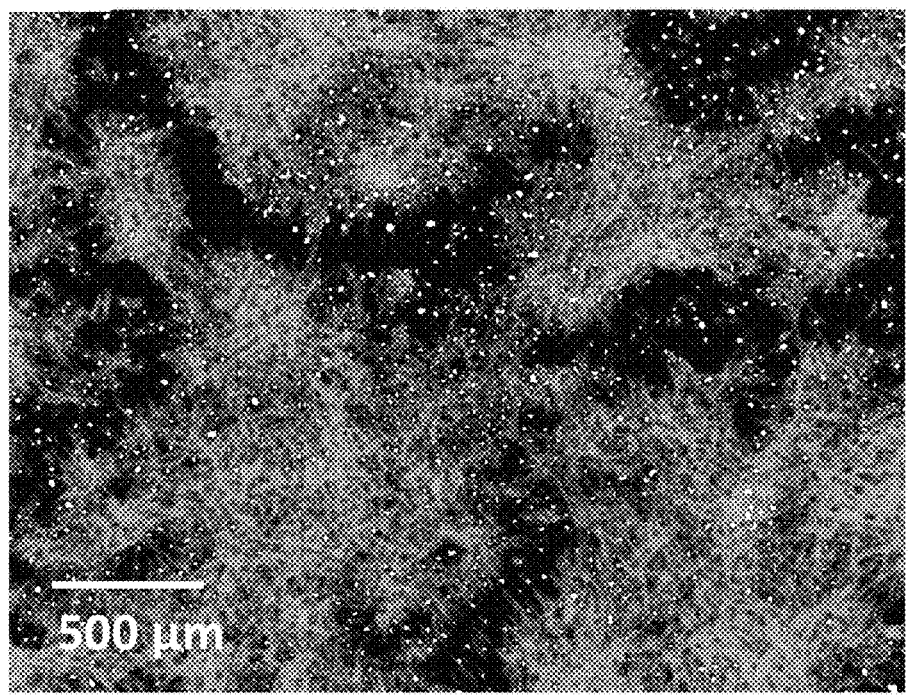
FIG. 2 is a fluorescent microscopy photograph of cell nuclei and cytoskeleton protein of human skin fibroblasts cultured for 7 days in a cell culture container described in Example 23.

Furthermore, when cells cultured for 7 days were stained with a fluorescent emission reagent and the form of the cell nuclei and the cytoskeletal protein were observed with a fluorescence microscope, the blue fluorescent cell nuclei (the white portions in FIG. 2) and the green fluorescent cytoskeletal protein (the gray portion in FIG. 2) were observed in a form in which the cells formed a colony in an overlapped state in the thickness direction three-dimensionally while accompanied by two-dimensional dense spots (refer to FIG. 2).

Figure 4:
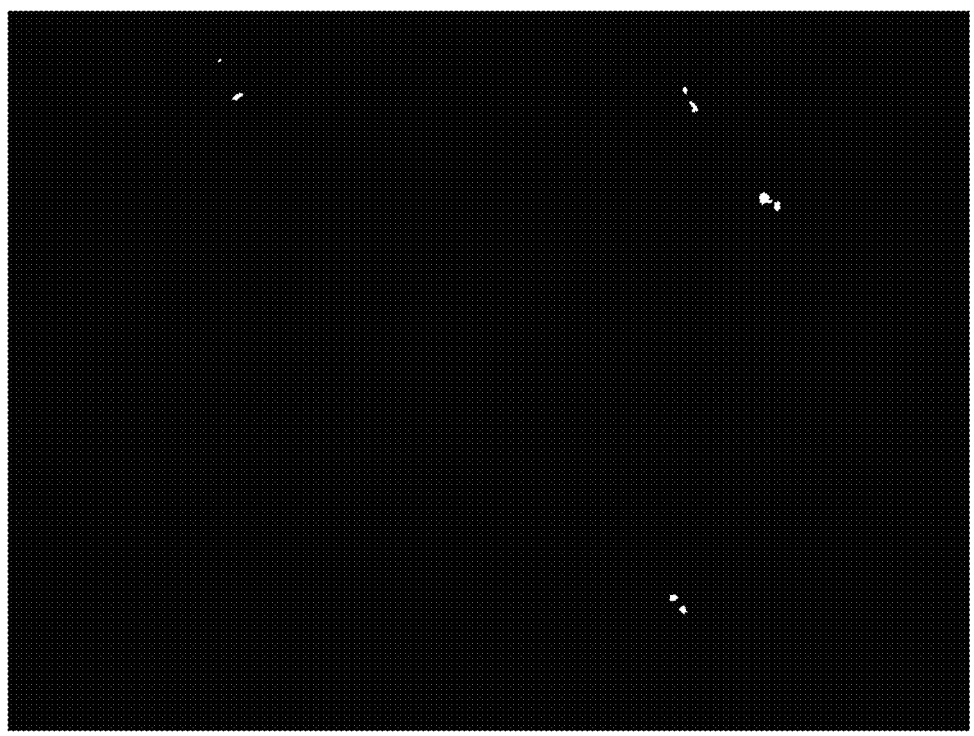
FIG. 4 is a fluorescent microscopy photograph in which the death autofluorescence emissions of human cultured cells which were cultured for 7 days in a cell culture container according to Example 23 are observed.

When evaluating the drug-metabolizing enzymes activity of these cultured cells in NADPH dehydrogenase, it was understood that almost 100% had drug metabolizing system enzyme activity similar to living cells. Furthermore, even when the autofluorescence was observed, since almost no fluorescence was observed, it was confirmed that 99.98% of the cultured cells were living cells in the same manner (refer to FIG. 4).

Example 24

Using the sterilized culture film 15 produced in Production Example 13, a thawed Hs-68 cell solution (1 mL) was inoculated according to the same method as Example 20. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.25±0.02 after 1 day passed, 0.78±0.04 after 3 days passed, and 1.80±0.09 after 7 days passed. The absorbance increased in a straight line over the passing days and change was not seen in the proliferation property even after 7 days passed. In addition, when observing the cells which were cultured for 7 days using the microscope, the cells proliferated in a state of forming a colony in the thickness direction and floated in a state of keeping a colony form when phosphate buffered physiological saline was added thereto.

When evaluating the drug-metabolizing enzymes activity of these cultured cells in NADPH dehydrogenase, it was understood that almost 100% had drug metabolizing system enzyme activity similar to living cells. Furthermore, when the autofluorescence was observed, it was confirmed that 100% of the cultured cells were living cells in the same manner.

Comparative Example 1

A thawed BALB/3T3 cell solution (1 mL) was inoculated on the hole section bottom surface of a 24-well TCPS multi-well plate (manufactured by Corning, the water contact angle was 46.1° after 15 seconds and 11.2° after 10 minutes) sterilized with γ rays. The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.27±0.03 after 1 day passed, 1.08±0.11 after 3 days passed, and 1.51±0.23 after 7 days passed. A tendency for the absorbance to gradually attenuate over the passing days was seen and the extent of the cell proliferation was reduced as the days passed. In addition, when observing the cells which were cultured for 7 days using the microscope, the cells proliferated in sheet form in an evenly planar state in the thickness direction and did not change in form or float even when phosphate buffered physiological saline was added thereto.

Comparative Example 2

A low-density polyethylene film (produced by Mitsui Chemicals, Inc., the water contact angle was 96.8° after 15 seconds and 59.5° after 10 minutes) was cut out in the same manner as the handling method of the culture film of the examples and sterilized. Next, the BALB/3T3 cells were cultured by the same method as in Example 1.

In the evaluation of the cell proliferation property by the WST-8 method, the absorbency was 0.22±0.02 after 1 day passed, 0.71±0.09 after 3 days passed, and 1.11±0.18 after 7 days passed. A tendency for the absorbance to gradually attenuate over the passing days was seen and the extent of the cell proliferation was reduced as the days passed. In addition, when observing the cells which were cultured for 7 days using the microscope, the cells proliferated in sheet form in an evenly planar state in the thickness direction and did not change in form or float even when phosphate buffered physiological saline was added thereto.

Comparative Example 3

Except that the monomer described in Production Example 1 was changed to 5-methyl-bicyclo[2.2.1]hept-2-ene (20.0 g) and 8-methyl-tetracyclo[4.4.0.1$^{2,5}$.1$^{7,10}$]-3-dodecene (32.2 g) and the solvent was changed to cyclohexane, a cyclohexane solution of poly(1-methyl cyclopentylene ethylene) and poly (3-methyl-tricyclo[4.3.0.1$^{2.5}$]decanylene ethylene) was obtained by the same method as in Production Example 1. The solution was filtered under pressure through a filter having a pore diameter of 5 μm, the solution was added to methanol, and a white polymer was filtered and dried to obtain 51 g of polymer 4. The hydrogenation rate is 100%, the weight average molecular weight (Mw) was 82000, the molecular weight distribution (Mw/Mn) was 2.26, and the glass transition temperature was 104° C.

Next, except for changing the solvent to cyclohexane, the culture film 11 with a thickness of 55 μm was produced using the same method as in Production Example 2. The water contact angle of the film was 92.1° after 15 seconds. Furthermore, the water contact angle was 55.4° after 10 minutes passed and the water contact angle was varied. Furthermore, the BALB/3T3 cells were cultured by the same method as in Example 1.

In the evaluation of the cell proliferation property by the WST-8 method, the absorbency was 0.20±0.04 after 1 day passed, 0.51±0.10 after 3 days passed, and 0.85±0.13 after 7 days passed. A tendency for the absorbance to gradually attenuate over the passing days was seen and the extent of the cell proliferation was reduced as the days passed. In addition, when observing the cells which were cultured for 7 days using the microscope, the cells proliferated in sheet form in an evenly planar state in the thickness direction and did not change in form or float even when phosphate buffered physiological saline was added thereto.

Comparative Example 4

The culture film 12 with a thickness of 200 μm was produced by hot pressing a Teflon® AF1600 (produced by Aldrich) powder under heating conditions of 200° C. and cut out and sterilized in the same manner as the handling method of the culture films of the Examples. The water contact angle at the time of substrate fabrication was 111.6° after 15 seconds. Furthermore, the water contact angle at the time of substrate fabrication was 110.3° after 10 minutes. Next, the BALB/3T3 cells were cultured by the same method as in Example 1.

In the evaluation of the cell proliferation property by the WST-8 method, the absorbency was 0.06±0.02 after 1 day passed, 0.14±0.11 after 3 days passed, and 0.18±0.09 after 7 days passed. A tendency for the absorbance to gradually attenuate over the passing days was seen and the extent of the cell proliferation was reduced as the days passed. In addition, when observing the cells which were cultured for 7 days using the microscope, the cells proliferated in a scattered manner and did not change in form or float even when phosphate buffered physiological saline was added thereto.

Comparative Example 5

A thawed BALB/3T3 cell solution (1 mL) was inoculated on a pattern surface of a hole section bottom surface of a sterilized 24-hole nano-culture plate (produced by S Co., Ltd., the water contact angle was 125° (after 15 seconds)). The same operation was carried out 9 times and 9 samples were prepared as the number of samples. After that, a lid was put thereon and the samples were moved to an incubator and culturing was started in sterilized air with an inside temperature at 37° C. and a carbonic acid gas concentration at 5%.

In the evaluation of the cell proliferation property by the WST-8 method, the absorbency was 0.07±0.03 after 1 day passed, 0.09±0.02 after 3 days passed, and 0.10±0.09 after 7 days passed. A tendency for the absorbance to gradually attenuate over the passing days was seen and the extent of the cell proliferation was reduced as the days passed. In addition, when observing the cells which were cultured for 7 days using the microscope, the cells proliferated by forming a colony in the thickness direction and did not change in form or float even when phosphate buffered physiological saline was added thereto.

Comparative Example 6

Except for changing the cell suspension to a Hs-68 cell solution (10 mL), culturing was started in sterilized air in an incubator with an inside temperature at 37° C. and a carbonic acid gas concentration at 5% in the same manner as Comparative Example 1.

In the evaluation of the cell proliferation property by the WST-8 method, the absorbency was 0.33±0.06 after 1 day passed, 1.49±0.11 after 3 days passed, and 3.10±0.13 after 7 days passed. A tendency for the absorbance to gradually attenuate over the passing days was seen and the extent of the cell proliferation was reduced as the days passed. In addition, when observing the cells which were cultured for 7 days using the microscope, the cells proliferated in sheet form and did not change in form or float even when trypsin-containing phosphate buffered physiological saline was added thereto.

Figure 3:
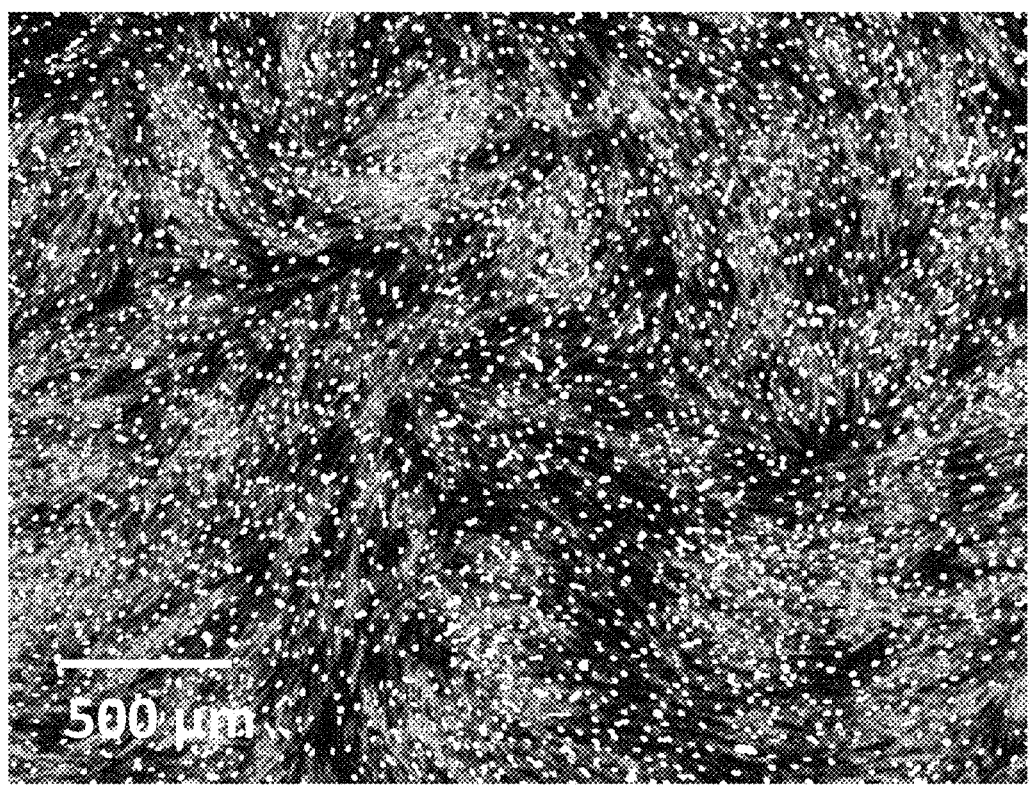
FIG. 3 is a fluorescent microscopy photograph of cell nuclei and cytoskeleton protein of human skin fibroblasts cultured for 7 days in a TCPS multi-well plate described in Comparative Example 6.

Furthermore, when cells cultured for 7 days were stained with a fluorescent emission reagent and the form of the cell nucleus and the cytoskeletal protein were observed with a fluorescence microscope, for the blue fluorescent cell nucleus (the white portion in FIG. 3) and the green fluorescent cytoskeletal protein (the gray portion in FIG. 3), the fluorescence distribution of the two-dimensionally spread sheet-shape was observed (see FIG. 3). It was impossible to confirm colony forming in which cells were overlapped in the thickness direction seen in the Hs-68 cells cultured in the cell culturing container described in Example 23.

When evaluating the drug-metabolizing enzymes activity of these cultured cells in NADPH dehydrogenase, it was understood that almost 0% had drug metabolizing system enzyme activity similar to living cells. Furthermore, it was impossible to measure the autofluorescence observation with the fluorescence absorption of a γ ray sterilized 24-hole TOPS multi-well plate, and evaluation was proved only using enzyme activity evaluation.

This application claims the benefit of priority based on Japanese Patent Application No. 2014-164912 filed on Aug. 13, 2014 and Japanese Patent Application No. 2015-019996 filed on Feb. 4, 2015, the entire disclosures of which are incorporated herein.

The invention claimed is:

1. A method for culturing cells, comprising:
a step of inoculating cells over a surface of a substrate of a medical instrument so as to be in contact with or held on the surface;
a step of obtaining cultured cells by culturing the cells; and
a step of floating the cultured cells from the surface by adding a buffer solution over the surface and then separating the cultured cells from the surface by adding a buffer solution over the surface on which the cultured cells are formed,
wherein the medical instrument comprises the substrate;
wherein cells are in contact with or held on the surface of the substrate, and
at least the surface of the substrate which holds the cells is formed of a fluorine-containing cyclic olefin polymer which contains a repeating structure unit represented by Formula (1),

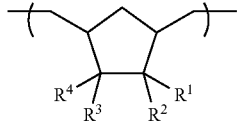

wherein in Formula (1), at least one of $R^1$ to $R^4$ is fluorine, an alkyl with 1 to 10 carbon atoms which contains fluorine, an alkoxy with 1 to 10 carbon atoms which contains fluorine, or an alkoxyalkyl with 2 to 10 carbon atoms which contains fluorine, $R^1$ to $R^4$ are selected from hydrogen, an alkyl with 1 to 10 carbon atoms, an alkoxy with 1 to 10 carbon atoms, or an alkoxyalkyl with 2 to 10 carbon atoms in a case where $R^1$ to $R^4$ are groups which do not contain fluorine, $R^1$ to $R^4$ may be the same as or different from each other, and $R^1$ to $R^4$ may be bonded to each other to form a cyclic structure,
wherein a water contact angle of the surface which is in contact with or holds cells is equal to or more than 80° and equal to or less than 110°,
wherein, in the step of obtaining cultured cells, the cells are proliferated so as to form a colony in the thickness direction,
wherein the medical instrument is a bag, a tube, a petri dish, a multi-well plate, or a flask, and
wherein at least the surface of the substrate which holds the cells is not provided with a convex-concave structure.

2. The method for culturing cells according to claim 1, wherein at least the surface of the substrate which is in contact with or holds cells is formed of a fluorine-containing cyclic olefin polymer composition which includes the fluorine-containing cyclic olefin polymer, a photocurable compound, and a photo-curing initiator.

3. The method for culturing cells according to claim 2, wherein a mass ratio of the fluorine-containing cyclic olefin polymer and the photocurable compound (fluorine-containing cyclic olefin polymer/photocurable compound) in the fluorine-containing cyclic olefin polymer composition is 99.9/0.1 to 50/50.

* * * * *